United States Patent [19]

Udovich et al.

[11] Patent Number: 5,210,353
[45] Date of Patent: May 11, 1993

[54] AROMATIC TRANSFORMATION PROCESS

[75] Inventors: Carl A. Udovich, Joliet; E. William Breder, Jr., Oak Forest; Ibrahim Ghanayem, Downers Grove; Mark W. Meszaros, Batavia; Thomas E. Nemo; Thomas G. Smith, both of Naperville, all of Ill.

[73] Assignee: Amoco Corporation, Chicago, Ill.

[21] Appl. No.: 620,529

[22] Filed: Nov. 30, 1990

[51] Int. Cl.$^5$ .......................... C07C 2/64; C07C 2/70; C07C 2/72; C07C 5/22

[52] U.S. Cl. .................................. 585/446; 585/459; 585/400; 585/428; 585/470

[58] Field of Search ............... 585/446, 459, 400, 428, 585/470

[56] References Cited

U.S. PATENT DOCUMENTS 3,321,540  5/1967  Trepka ................................. 585/428
4,929,785  5/1990  Hussain ............................... 585/428

Primary Examiner—Anthony McFarlane
Assistant Examiner—Nhat Phan
Attorney, Agent, or Firm—Thomas E. Nemo; William H. Magidson; Frank J. Sroka

[57] ABSTRACT

A process is provided for transaralkylating a class of starting compounds comprised of aryl-substituted lower alkanes and aryl-substituted fused alkylene ring compounds to produce derivatives of such compounds wherein benzyl substituents thereof have different alkyl substituents compared to the starting compounds. The process is carried out by admixing such a starting compound with a lower alkyl-substituted aromatic compound under liquid phase conditions in the presence of a catalytically effective amount of a Friedel-Crafts catalyst. The process makes possible new and economical routes for synthesizing desired lower alkyl-substituted benzyl group containing compounds, such as 2,2-di(-lower alkyl-substituted) phenyl propanes and 1,3,3-trimethyl-1-(lower alkyl-substituted)-phenyl indans. Thus, there is provided a three-step process for making dixylylpropane from alpha methyl styrene and also a two-step process for making 1,3,3,6-tetramethyl-1-o-xylyl indan from alpha-4-dimethyl styrene. Provided also is a process for preparing 3,3′,4,4′-dixylylmethane from a mixture of isomeric dixylylmethanes.

29 Claims, 1 Drawing Sheet

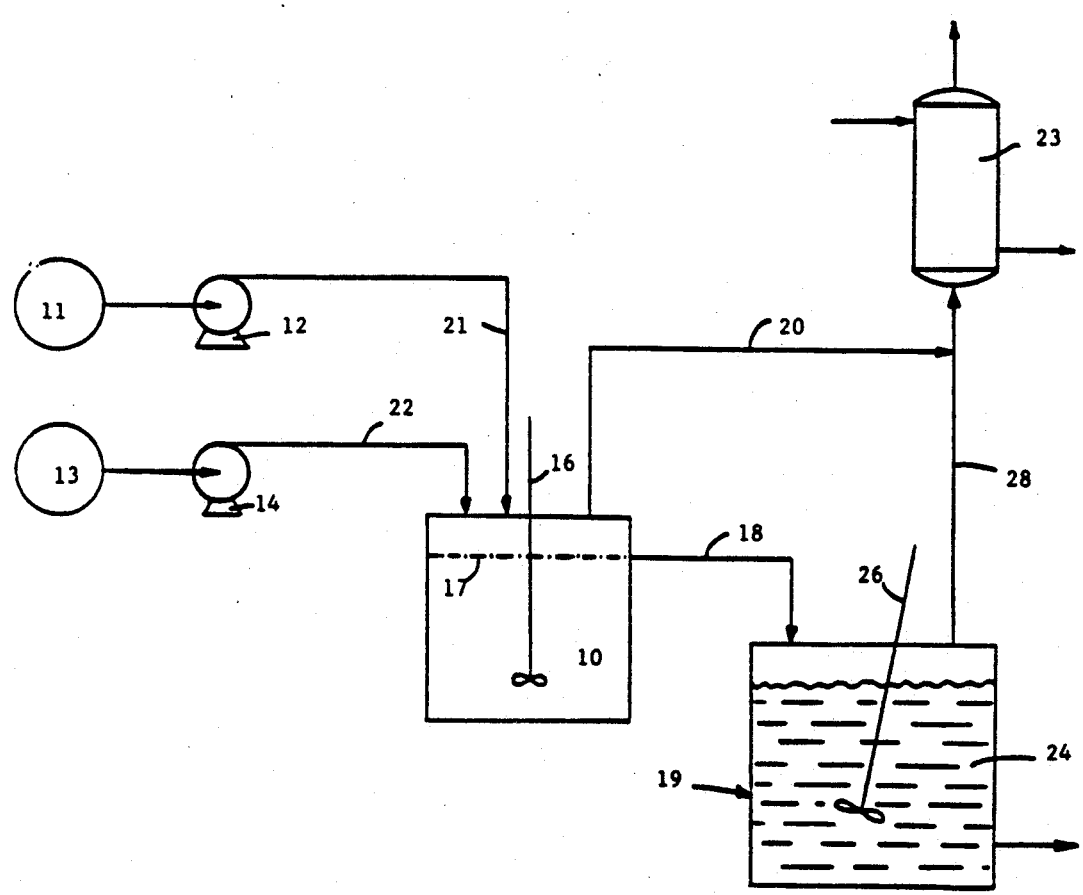

AROMATIC TRANSFORMATION PROCESS

FIELD OF THE INVENTION

This invention relates to a transformation process for aromatics. In a particular aspect, this invention pertains to methods for preparing certain alkaryl-substituted alkanes and 1-alkaryl-substituted indans.

BACKGROUND OF THE INVENTION

A variety of useful high performance polymers, or so-called engineering resins, are prepared by polymerizing various polymerizable carboxy-substituted arylene compounds. Accordingly, there exists considerable interest in commercially practical, efficient synthetic methods which can be used to prepare such compounds from low cost starting materials. Heretofore known methods are generally inefficient and/or excessively costly.

For example, isopropylidene bis(phthalic acid) (IBPA), also known as 2,2-bis(3,4-dicarboxyphenyl) propane, and its anhydride, isopropylidene bis(phthalic anhydride) (IPAN), are polymerizable into polymers that are useful for blending with polyether ketone and polyimide resins. These particular compounds can be prepared by oxidizing 2,2-dixylyl propane, also known as isopropylidene bis(xylene) and as 2,2-bis-(3,4-dimethylphenyl) propane (DXP).

DXP can be prepared by a known method involving the Friedel-Crafts coupling of o-xylene with 2,2-dichloro propane, as disclosed in U.S. Pat. No. 2,712,543 to Gresham et al.

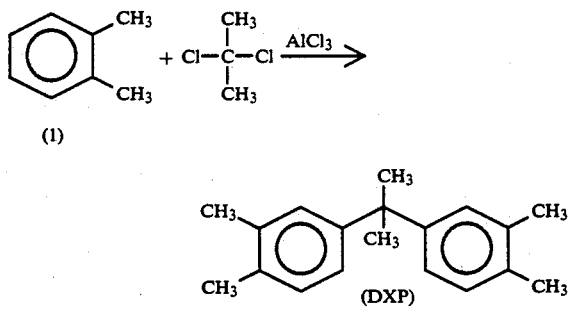

(1)

This reaction does produce about a 50 percent yield of DXP, but this route is impractical because of the prohibitive cost of 2,2-dichloro propane.

As another example, phenylindantricarboxylic acids, such as 1,3,3-trimethyl-6-carboxy-1-(3',4'-dicarboxyphenyl)indan, and its mixed acid anhydride, which are polymerizable into polymers useful for blending with polyether ketone and polyimide resins, can be prepared by oxidizing 1,3,3,6-tetramethyl-1-o-xylyl indan (TMXI).

No commercially practical synthetic route(s) or method(s) are known to the prior art for making commercial-scale quantities of TMXI.

A compound such as alpha-methyl styrene is available in commercial quantities and at a unit price which is not prohibitive. Alpha-methyl styrene can be reacted with hydrogen chloride to form the hydrochloride which in turn can be coupled with o-xylene to form 2-phenyl-2-xylyl propane (PXP). However, prior to the present invention, no commercially practical method was known by which 2-phenyl-2-xylyl propane could be converted into 2,2-dixylyl propane, so far as is now known.

Similarly, a compound such as alpha-4-dimethyl styrene is available in commercial quantities and at a unit price which is not prohibitive. Alpha-4-dimethyl styrene can be dimerized to produce 1,3,3,6-tetramethyl-1-p-tolyl indan. However, prior to the present invention, no commercially practical method was known by which 1,3,3,6-tetramethyl-1-p-tolyl indan could be converted into 1,3,3,6-tetramethyl-1-o-xylyl indan, so far as is now known.

Previously, it was reported [C. Serres and E. K. Fields, JACS, 88:4685 (1960)] that, in benzylation reactions catalyzed by aluminum chloride, the expected benzylation product is formed first and then undergoes transaralkylation (debenzylation and rebenzylation) with arene solvents. In addition, U.S. Pat. No. 3,043,886 teaches that a polyarylmethane can be reacted with an aromatic hydrocarbon (preferably the same aromatic hydrocarbon used to prepare the diarylmethane) in the presence of a Lewis acid to produce diaryl methanes. Also, it was reported by R. H. Allen et al., JACS, 81:42 (1958) that, in a solution of p-t-butyl toluene in o-xylene at 0° C. having a weight ratio of 1:9 and containing aluminum chloride, the t-butyl group could be transferred to o-xylene without isomerizing p-t-butyl toluene. Olah et al, J. Org. Chem., 29:2310 (1964); 29:2313 (1964); and 29:1315 (1964); carried out Friedel-Crafts isomerizations of various substituted toluene and dialkylbenzenes, and demonstrated that isomerization in aromatic hydrocarbon solvents is entirely a dealkylation-realkylation process.

However, so far as now known, no one has previously transaralkylated a benzyl group in a diaryl-substituted lower alkane, such as a 2,2-diaryl propane, or in an aryl-substituted fused alkylene ring compound, such as a 1-aryl indan, to produce lower alkyl-substituted phenyl-substituted derivatives thereof. Such derivatives are suitable for oxidation to produce the corresponding carboxylated aryl alkanes and aryl carboxylated indan products.

A new and commercially practical method of preparing, for example, alkaryl-substituted propane-type compounds, such as 2,2-bis(lower alkyl-substituted phenyl) propanes, 1-(lower alkyl-substituted) phenyl indans, 2,2-bis(lower alkyl-substituted phenyl) methanes, and the like, from relatively low cost starting materials, would be economically advantageous. The present invention provides such a method.

SUMMARY OF THE INVENTION

The present invention provides a method for selectively changing the lower alkyl substituents, or the positions thereof, in aryl rings of bis(aryl) alkanes (i.e., transaralkylating) by contacting, under liquid phase conditions, a bis(aryl) alkane with a molar excess of an alkyl-substituted aromatic compound in the presence of a catalytically effective amount of a Friedel-Crafts catalyst.

A present preference is to employ as the bis(aryl) alkane either an aryl-substituted lower alkane or an aryl-substituted, fused lower alkylene ring compound, such as a 1-aryl-substituted indan.

Thus, the present invention comprises a method for transaralkylating a bis(aryl)alkane which method comprises contacting, under liquid phase conditions, said bis(aryl)alkane with a molar excess of an alkyl-substituted aromatic compound having different alkyl substitution from at least one of the aryl groups of said bis(aryl)alkane, said contacting being carried out in the presence of a catalytically effective amount of a Friedel-Crafts catalyst for a time period sufficient to replace at least some of said aryl groups of said bis(aryl)alkane with said alkyl-substituted aromatic, wherein said bis(aryl)alkane is characterized by the formula:

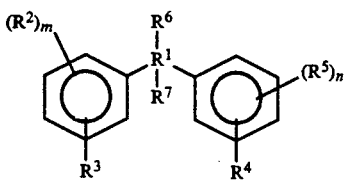

(1)

and wherein:

$R^1$ is a carbon atom, $R^2$ and $R^5$ are each a lower alkyl radical, $R^3$, $R^4$ and $R^6$ are each independently selected from the group consisting of hydrogen and a lower alkyl radical, $R^7$ is a lower alkyl radical, and, in addition, when $R^3$ is in the 2-position in Formula (1), $R^3$ and $R^7$ together may also represent an alkylene radical containing up to four carbon atoms, inclusive, and m and n each is an integer having a value of 0 through 4, inclusive.

When $R^3$ is in the 2-position and together with $R^7$ represents an alkylene radical, the alkylene radical can be branched or unbranched.

The term "lower" as used herein particularly in reference to "alkyl" and to "alkylene" has reference to a carbon chain containing up to 4 carbon atoms, inclusive.

One presently preferred class of Formula (1) compounds comprises 2,2-di(aryl)propanes wherein $R^2$ and $R^3$ are each methyl, $R^4$ is hydrogen, $R^6$ and $R^7$ are each methyl, m is 1, and n is 0.

Another presently preferred class of Formula (1) starting compounds comprises 1-aryl indans. For these compounds in Formula (1) $R^2$ is methyl, $R^4$ is methyl, $R^6$ is methyl, $R^3$ is in the 2-position and together with $R^7$ forms 2,2-dimethylethylene, and m is 1 and n is 0.

One aspect of the method of this invention involves transaralkylation of a benzyl group in a Formula (1) compound with an alkyl-substituted aromatic compound, such as, for example, is illustrated by the following equation:

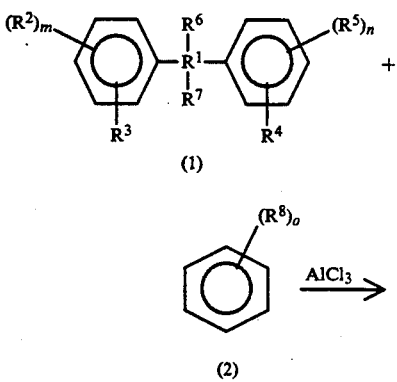

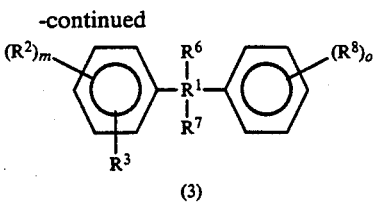

(3)

The aromatic compound represented by Formula (2) is present in a stoichiometric excess vis-a-vis the compound of Formula (1) and can be regarded as characterizing a class of suitable transformation agents. In Formula (2), $R^8$ is a lower alkyl radical (preferably methyl), and o is an integer having a value of 1 through 5, inclusive. A present preference for o is 2.

The present transformation method is practiced by admixing a Formula (1) compound with a transformation agent, such as an alkyl-substituted aromatic compound represented by Formula (2) (above), under liquid phase conditions in the presence of a catalytically effective amount of a Friedel-Crafts catalyst, such as a catalyst preferably comprising $AlCl_3$ or an approximately equimolar mixture of $AlCl_3$ and HCl. Other suitable Friedel-Crafts catalysts include, for example, $AlBr_3$, $SbX_5$, $FeX_3$, $TiX_4$, $SnX_4$ and other known Lewis Acids, wherein X is a halogen and preferably bromine or chlorine. A molar excess of the transformation agent, which excess is preferably at least about 10 times the molar quantity of the Formula (1) compound, is used.

In a transformed product compound represented by Formula (3), above, the phenyl group previously substituted by $(R^5)_n$ and $R^4$ is replaced by a phenyl group substituted by $(R^8)_o$ derived from the selected transformation agent represented by Formula (2).

One principal advantage of this particular transformation method is that it permits one to convert readily available, and/or relatively inexpensively synthesized, starting benzyl group-containing compounds into less readily available compounds, such as lower alkyl-substituted benzyl group-containing compounds, using a relatively simple Friedel-Crafts type catalyzed reaction. Various relatively inexpensive lower alkyl-substituted aromatic compounds can thus be used as initial materials for the preparation of such lower alkyl-substituted benzyl group-containing compounds. A variety of transformed aromatic products can be prepared by the practice of the present invention. However, one presently preferred class of transformed products comprises aromatic ring alkylated products which can be subsequently oxidized into polycarboxylic acids wherein the carboxyl groups are ring substituted on aromatic nuclei, such as bis(methyl-substituted) aryl alkanes. Presently preferred such transaralkylated products include, for example, 2,2-di(alkaryl) propanes, 1-alkaryl indans, di(alkaryl) ethanes and like polyalkylated bis(aryl) alkanes, all of which are useful as feedstocks for subsequent oxidation of the alkyl groups into carboxyl groups. The resulting carboxyl substituted products are useful as polymerizable monomers in the synthesis of polymers with high performance characteristics.

For example, a starting diaryl propane can be transaralkylated by the process of the present invention to produce a wide variety of bis(alkaryl-substituted) propanes. Also, a starting 1-aryl indan, for another example, can be transaralkylated by the process of the present invention to produce a wide variety of 1-alkaryl-substituted indans.

Another principal advantage of this transaralkylation process is that it can be combined as a method step with another or other process steps. Thus, the present invention provides a family of various new and commercially promising synthetic routes suitable for the preparation of bis(aryl) alkanes such as, for example, the various bis(alkyl-substituted)aryl propanes, 1-(alkyl-substituted)-phenyl indans, and bis(alkyl-substituted) aryl ethanes as above indicated, from relatively inexpensive starting materials using the transaralkylation process of this invention as one step of a preparation procedure. So far as now known, members of such classes of exemplary compounds cannot be as economically and/or as easily prepared by prior art techniques.

Thus, for one example, the present invention makes possible a new route for preparing 2,2-di(3',4'-dimethyl)phenyl propane and other diaryl propanes from alpha methyl styrene and the like, as hereinbelow described.

For another example, the present invention makes possible a new route for preparing 1,3,3,6-tetramethyl-1-o-xylyl indan and other 1-aryl-substituted indans from alpha-4-dimethyl styrene and the like, as hereinbelow described.

For another example, the present invention makes possible the preparation of 3,3',4,4'-dixylylmethane from 2,3',3,4'-dixylylmethane, 2,2',3,3'-dixylylmethane or from mixtures of these compounds. A particularly useful method of this invention is the method for the preparation of relatively pure 3,3',4,4'-dixylylmethane from a mixture of 3,3',4,4'-, 2,3',3,4'- and 2,2',3,3'-dixylylmethane. This mixture is readily obtained by the acid catalyzed condensation of o-xylene using a source of formaldehyde, e.g. paraformaldehyde, trioxane or aqueous formaldehyde, as the coupling agent. However, this mixture of compounds is not desirable for subsequent oxidation to the corresponding tetracarboxylic acids due to the difficulty in separating these acids. Consequently, it is important to separate the desired 3,3',4,4'-dixylylmethane isomer from the other isomers prior to the oxidation reaction. The 3,3',4,4'-dixylylmethane isomer in a pure form is highly desirable because it is a valuable feedstock for preparing by an oxidation process, benzophenonetetracarboxylic acid, a monomer used for high performance imide polymers.

Using the transaralkylation method of this invention, the less desirable mixture of 2,2',3,3'-, 2,3',3,4'- and 3,3',4,4'-dixylmethane is contacted with a molar excess of o-xylene as a transaralkylation agent, in the presence of a Friedel-Crafts catalyst such as aluminum chloride, and this mixture is converted for the most part, to relatively pure 3,3',4,4'-dixylylmethane which can be readily isolated.

The present invention also provides in one aspect a new and very useful continuous process for alkylating an alkyl-substituted aromatic compound with certain 2-phenyl-2-chloro propanes in the presence of a Friedel-Crafts catalyst to produce 2-phenyl-2-aryl propanes that are useful as feedstocks for transaralkylating in accord with teachings of the present invention.

Presently preferred transaralkylated products produced by the processes of this invention are compounds containing poly (lower alkyl-substituted) phenyl groups associated with a substituted propane, a 1-aryl-substituted indan, and other diaryl alkanes.

Transaralkylated products produced by the processes of this invention can be purified using, if desired, conventional recovery procedures involving distillation and crystallization. However, in one further aspect, the present invention also provides preferred product recovery procedures.

Oxidation and dehydration procedures known to the prior art can be employed to produce the corresponding carboxyl substituted and carboxylic acid anhydride derivatives from transaralkylated products produced by the present transaralkylation invention. As such, these prior art procedures are not part of the present invention. Such derivative acids, and their anhydrides, are polymerizable to form polymers which are useful as resins and as blending agents for compounding with so-called engineering resins.

Various other and further features, embodiments, and the like which are associated with the present invention will become apparent and better understood to those skilled in the art from the present description considered in conjunction with the accompanying drawing wherein presently preferred embodiments of the invention are illustrated by way of example. It is to be expressly understood, however, that the drawing and the associated accompanying portions of this specification are provided for purposes of illustration and description only, and are not intended as limitations on the invention.

BRIEF DESCRIPTION OF THE DRAWING

In the accompanying drawing forming part of the specification:

FIG. 1 is a flow diagram for a continuous process embodiment of this invention for alkylation using 2-phenyl-2-chloro propane to produce 2-phenyl-2-xylylpropane, a starting material for transaralkylation in accord with the present invention.

DETAILED DESCRIPTION OF PREFERRED EMBODIMENTS

Transformation Conditions and Products

It is theorized that the present transformation/transaralkylation process involves debenzylation followed by rebenzylation, but there is no intent herein to be bound by theory. In operation, a transformation agent, i.e., an alkylated aromatic compound, such as, for example, a compound of Formula (2) above, whose existing alkyl substitution is to be substituted or transferred into a bis(aryl)alkane compound of Formula (1), above, is combined, preferably in a molar excess, as indicated above, with such bis(aryl)alkane in the presence of a Friedel-Crafts catalyst.

The transformation process of this invention is carried out under liquid phase conditions, preferably at ambient temperatures and pressures, in the presence of a catalytically effective amount of a Friedel-Crafts catalyst, such as $AlCl_3$ or the like. This method can also be practiced at elevated temperatures; however, in such an event the formation of undesirable indans may be increased. $AlCl_3$ is used preferably in combination with HCl in approximately equimolar proportions, as indicated above. While, in general, the catalytically effective quantity of $AlCl_3$ employed in a given transaralkylation is preferably in the range of from about 5 to 25 mole percent based on starting bis(aryl)alkane, larger and smaller amounts of this catalyst can be employed without departing from the spirit and scope of this invention. In the present most preferred practice of this invention, the amount of $AlCl_3$ employed is about 10–20 mole percent (same basis).

The contemplated transformation process appears to involve an equilibrium reaction. Thus, the amount of transaralkylation achieved (or the yield of desired transaralkylated compound produced) in respect to a given starting bis(aryl)alkane using a given transaralkylation agent is enhanced by the use of a molar excess of such transaralkylation agent. The processing time usually is in the range of about 1 to 3 hours, and the yield generally is about 40 to 45 percent.

During the occurrence of a transaralkylation reaction, certain competitive reactions may occur, such as are typical of carbonium ion chemistry generally, and such reactions can operate both to affect the yield of a desired or desirable product, and also to influence the nature and extent of the by-products produced. For a specific example, when phenyl xylyl propane (PXP) is transaralkylated with o-xylene in the presence of a Friedel-Crafts catalyst as taught herein (see particularly teachings hereinbelow), in addition to the reverse recombination reaction of benzene with the cumyl carbocation, the following side reactions have been observed:

1. Hydride Abstraction.

The intermediate carbocation abstracts a hydride from one or more of the system components to generate 3,4-dimethyl cumene. Hydride abstraction is a major competitive reaction, the rate of which is significantly affected by the concentration of Lewis Acid used in the Friedel-Craft catalyzed alkylation step.

2. Dimerization (Indans).

The intermediate carbocation can attack any free olefin (such as alpha-3,4-trimethyl styrene or alpha methyl styrene) to form a dimer cation which upon internal attack on an aromatic ring forms indans. A variety of indans, such as 1,3,3,5,6-pentamethyl-1-phenylindan, 1,3,3-trimethyl-1-phenylindan, 1,3,3-trimethyl-1-(3',4'-dimethylphenyl) indan, etc., are produced when carbocation and olefin are present.

3. Indenes.

Consequent to indan formation, dearylation may occur by an analogous mechanism involving formation of a stable benzylic carbocation. Loss of a proton from the benzylic carbocation results in an indene.

4. Spiroindans.

Consequent to indan and indene formation, continued competitive reactions involving olefin isomerization and carbocation addition to isomerized olefins produce spiroindans. When excessive times are allowed for transaralkylation, spiroindans were observed to be formed at levels of near 10 percent.

5. Stability of DXP.

Competitive reactions having similar energies of activation readily occur. Since PXP and DXP are so similar, reactions involving transaralkylation as well as by-product formation should be essentially indistinguishable. The stability of DXP has been evaluated under typical transaralkylation conditions with catalyst loadings of ½ what is now believed to be a preferred and normal value (about 20 mole percent based on DXP), twice such normal value, and five times such normal value using aluminum chloride catalyst levels. The diarylpropanes are believed to be dynamically reactive in the presence of aluminum chloride. Under such a normal catalyst loading (20 mole percent), a sample which initially contained 95 percent pure DXP (5 percent PXP) suffered a reduction in DXP concentration to near 75 percent after four hours at room temperature.

Although several minor by-products were observed to be formed, the two major degradation products are 3,4-dimethylcumene and 1,3,3,5,6-pentamethylindene. The cumene derivative is theorized to be formed by some hydride transfer scheme involving an intermediate (type) carbonium ion whereas the indene is theorized to originate from dearylation of 1,3,3,5,6-pentamethyl-1-(3'4'-dimethylphenyl)-indan (the indan being the dimer of 3,4-dimethyl-alpha-methyl styrene). Doubling the normal (20 mole percent) concentration of $AlCl_3$ (to 40 mole percent) caused the level of DXP to be reduced from about 95 percent to about 35 percent after four hours at room temperature, while 3,4-dimethylcumene levels concurrently rose to near 30 percent and indan levels to 20 percent. The presence of alpha-3,4-trimethyl styrene was also observed.

At 5 times such normal $AlCl_3$ concentration (molar equivalence with DXP), the amount of DXP remaining after 4 hours is only 5 percent. Levels of cumene increase to greater than 40 percent while indan levels rise to near 30 percent.

6. Effect of Benzene on DXP Production.

The transaralkylation step for the synthesis of DXP involves the exchange of benzene with o-xylene in a system containing, for example, a 5:1 ratio of o-xylene to PXP. Complete conversion and exchange of o-xylene for benzene would result in a final solvent-reactant medium containing a 4:1 ratio of xylene:benzene. Since there is little apparent difference, respectively, between xylene's and benzene's ability to be alkylated by in-situ generated carbocations, it is difficult to push the reaction to completion without removal of benzene. The overall stability of DXP in solvent systems containing various loadings of benzene was evaluated to determine the effect of the presence of benzene. Solvent ratios of o-xylene/benzene of 20/1, 10/1 and 5/1, were evaluated, and the results were substantially unaffected and were analogous to that observed at similar $AlCl_3$ levels when benzene is absent. The only difference in generated product profile is an enhanced level of PXP which is expected as the levels of benzene increase. The overall sum of PXP and DXP appears to be additively constant.

In spite of the foregoing side reactions, when the herein described conditions for transaralkylation are employed, such as the conditions hereinbelow described for PXP transaralkylation, commercially significant and practical yields of desired transaralkylated products are achievable, such as about 30 to about 40 mole percent DXP based on starting PXP, for example.

In general, the product of the transaralkylation process of this invention is characteristically a liquid mixture that is separable from a second, dense phase catalyst layer which can be reused, if desired.

A product separation and purification procedure is carried out when a purified product is desired.

In preferred operational modes, the present invention provides processes for preparing 2,2-di(lower alkyl-substituted) aryl propanes, and 1-(lower alkyl-substituted) aryl indans, as now described.

Transaralkylation of 2,2-Diaryl Propanes

By the process of the present invention, any starting 2,2-diaryl propane is transaralkylatable to produce a wide variety of substituted propanes.

Presently preferred starting 2,2-diaryl propanes for use in transaralkylation are as above characterized. With such starting 2,2-diaryl propanes, the transaralkylation process can be represented by the following exemplary equation:

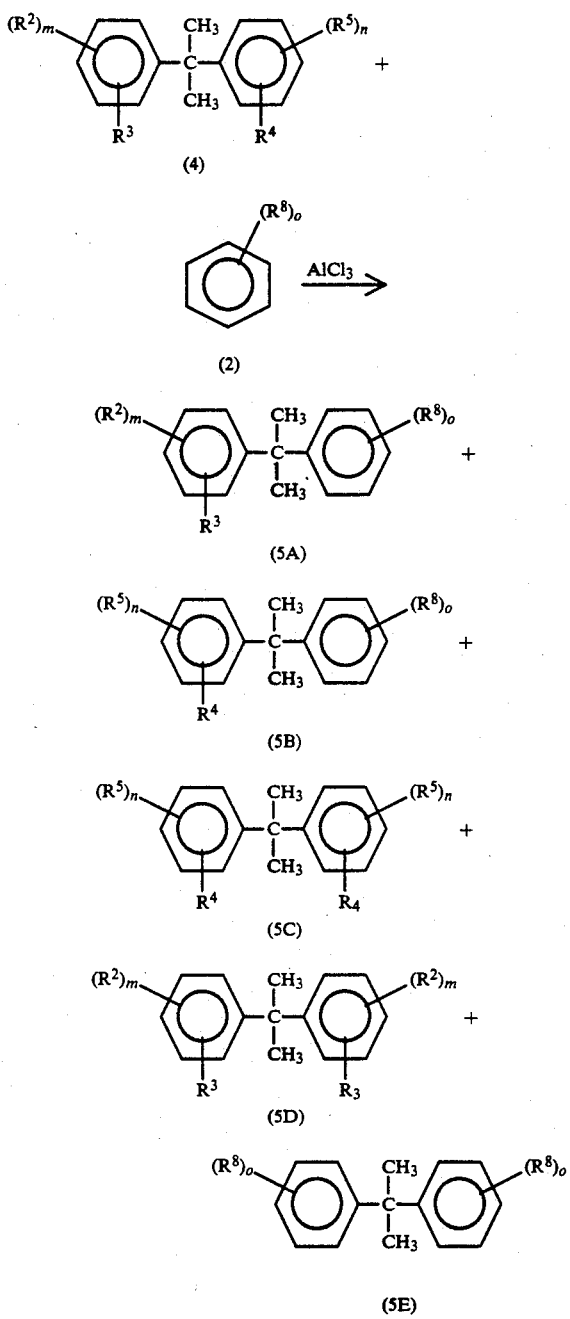

wherein the starting compound represented by Formula (4), which compound is a Formula (1) compound where $R^6$ and $R^7$ are each methyl, and the transaralkylation agent is represented by Formula (2). The transaralkylated products are represented by Formulas 5A–5E, wherein 5A and 5B are the desired products.

Compared to prior art methods of preparing 2,2-diaryl propanes, such as above herein reviewed, the present invention permits one to employ much more readily available and less costly reagents to prepare starting 2,2-diaryl propanes, such as those of Formula (4), which are then transaralkylatable as taught herein to obtain a desired product 2,2-diaryl propane, such as one of Formula (5A).

For example, the relatively inexpensive and commercially available compound, alpha-methyl styrene, is reacted with hydrogen chloride to form the hydrochloride which addition follows Markovnikov's rule. Such addition product, in turn, is coupled with a methyl-substituted benzene preferably selected from the group consisting of toluene and xylene (most preferably o-xylene) under Friedel-Crafts catalysis and reaction conditions. The toluene or the o-xylene are likewise relatively inexpensive and commercially available. The preferred product thus formed (depending upon the respective starting material used) is either 2-phenyl-2-tolyl propane or 2-phenyl-2-xylylpropane (PXP). The synthesis for the preferred product (PXP) is represented by the following equation:

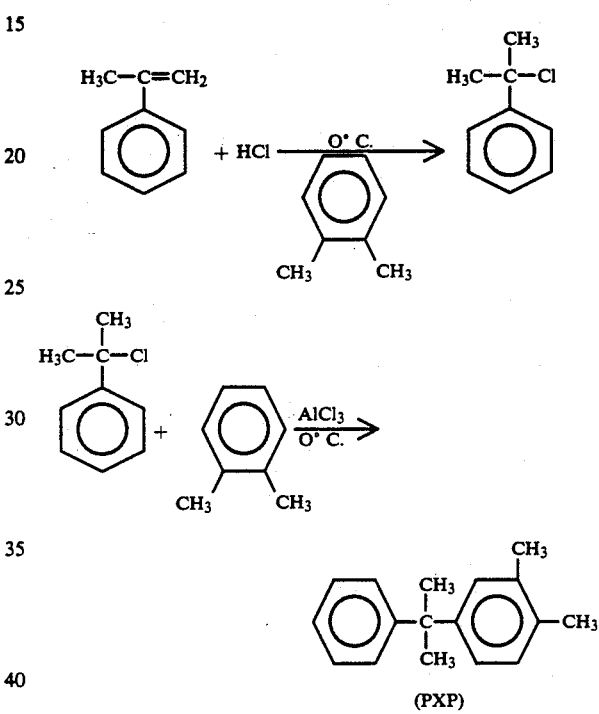

The hydrochlorination and coupling reactions illustrated by the respective preceding illustrative equations are conveniently and preferably carried out in the same reactor. Also, the same solvent, preferably o-xylene, is preferably and conveniently always used in both reactions.

The product bis(aryl) propane (preferably PXP) is then transaralkylated in accord with the present invention using conditions such as generally indicated above (liquid phase, room temperature conditions in a molar excess of transaralkylation agent which is preferably a methyl-substituted benzene), preferably using the same respective methyl-substituted benzene as employed in the preceding coupling reaction, (for example, o-xylene when making the preferred DXP product) to form the transaralkylated product (which is preferably 2,2-dixylyl propane (DXP)):

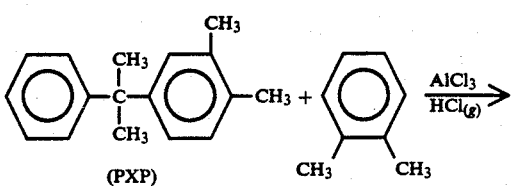

-continued

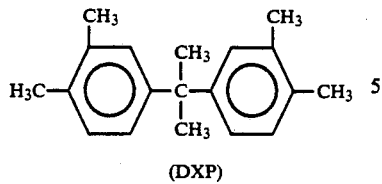
(DXP)

Particularly preferred is an o-xylene/PXP molar ratio of about 5 in the presence of about 20 mole percent AlCl₃, based on PXP.

Procedures for recovery of the transaralkylated product are provided below.

1-Aryl Indans

By the process of the present invention, any starting 1-aryl indan is transaralkylatable to produce a wide variety of 1-(alkyl-substituted) aryl indans.

Presently preferred starting 1-aryl indans for use in transaralkylation are as above indicated and are producible from certain starting materials as taught herein. With such a starting 1-aryl indan, the transaralkylation process can be represented by the following generic exemplary equation:

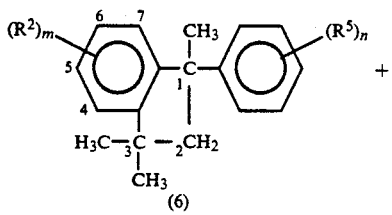
(6)

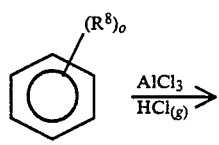
(2)

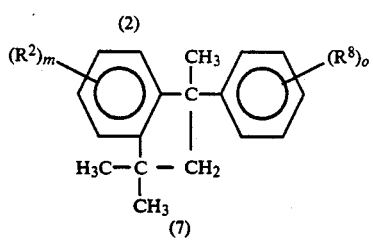
(7)

wherein the starting compound is represented by Formula (6), the transaralkylation agent is represented by Formula (2), and the transaralkylated product compound is represented by Formula (7). In such Formulas (2), (6) and (7), each of $R^2$, $R^5$, $R^8$, n, m, and o has its respective above defined meaning (see definitions for Formulas (1) and (2)). $R^8$ is preferably methyl.

Compared to prior art methods in preparing alkyl-substituted aryl nuclei in the 1-position of the indan ring structure, the present invention permits one to employ readily available and less costly reagents for preparation. Thus, such starting 1-aryl indans are initially conveniently and preferably synthesized by the acid catalyzed dimerization of alpha-methyl styrene (preferably lower alkyl-substituted):

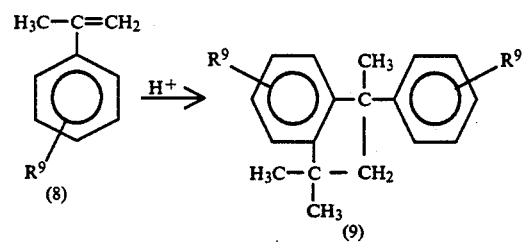
(8) (9)

wherein the starting alkyl-substituted alpha methyl styrene compound is represented by Formula (8) and the product 1-aryl indan compound is represented by Formula (9). $R^9$ in each such formula is hydrogen or a lower alkyl radical (preferably methyl). The position of $R^9$ in a compound of Formula (9) is determined by the position of $R^9$ in the compound of Formula (8) used to make such formula (9) compound; thus, both the indan phenyl group and the 1-phenyl group preferably have the same substituent $R^9$ groups. For example, when alpha-4-dimethylstyrene is dimerized, 1,3,3,6-tetramethyl-1-p-tolyl indan is obtained as shown below:

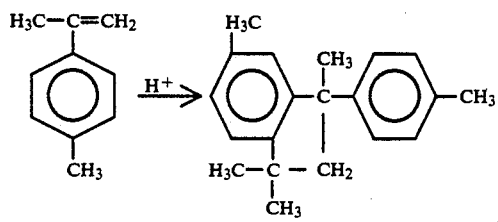

The simultaneous acid catalyzed dimerization of more than one styrene monomer leads to a complex array of products:

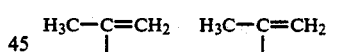
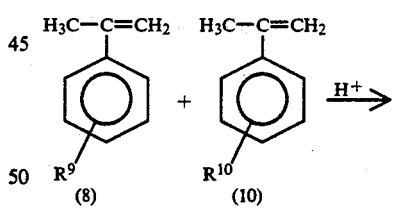
(8) (10)

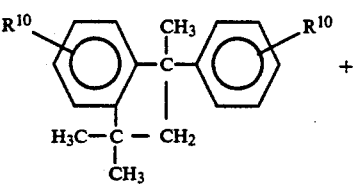
+

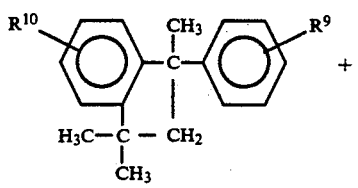
+

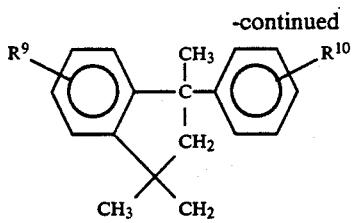

wherein the starting alkyl-substituted alpha methyl styrene compounds are represented by Formula (8) (as defined above) and by Formula (10) (wherein the $R^{10}$ substituent is hydrogen or a lower alkyl radical provided that in any given such dimerization reaction $R^{10}$ is different from $R^9$).

Such a product array is difficult to separate into individual components. Thus, it presently appears to be impractical (and not desired) to use this mixed styrene monomer synthesis route to prepare pure 1-(alkyl-substituted) aryl indans wherein the indan-phenyl group and the 1-phenyl group have different alkyl substituents.

As compared to the dimerization procedure illustrated by the preceding equation, transaralkylation by the present invention (as taught above) provides a substantially improved and presently preferred technique for preparing 1-phenyl indans wherein the indan-phenyl group and the 1-phenyl group have different respective substituent alkyl groups. Thus, in such a presently preferred synthesis for making alkyl-substituted 1-aryl indans by the present invention, preferably only a single type of alpha-methyl styrene starting material is dimerized, such as, for example, alpha-4-dimethyl styrene, as above illustrated, and the resulting 1-aryl indan produced, such as, for example, 1,3,3,6-tetramethyl-1-p-tolyl indan, is then selectively substituted by transaralkylation on the aryl group in the 1-position to form other desired 1-alkaryl derivatives as illustrated by the following equation:

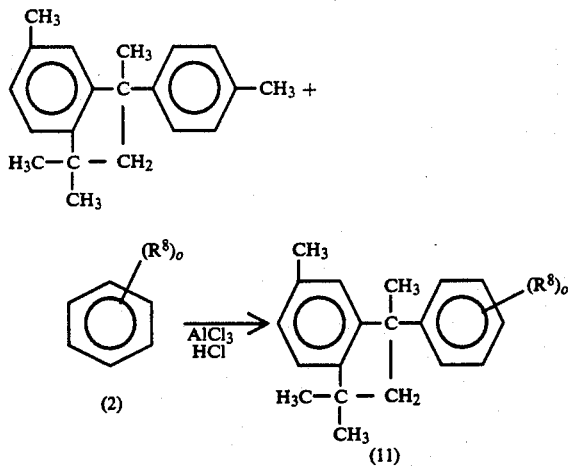

wherein Formula (2) and its substituents remain the same as above defined and wherein the product 1,3,3,6-tetramethyl-1-(lower alkyl-substituted)phenyl indan is represented by Formula (11). In Formula (11), $R^8$ and o remain as defined above for Formula (2). Preferably $R^8$ is methyl.

When, for example, o-xylene (presently preferred) is employed as the methyl-substituted benzene transaralkylation agent for 1,3,3,6-tetramethyl-1-p-tolyl indan, the transaralkylated product is 1,3,3,6-tetramethyl-1-o-xylyl indan (TMXI):

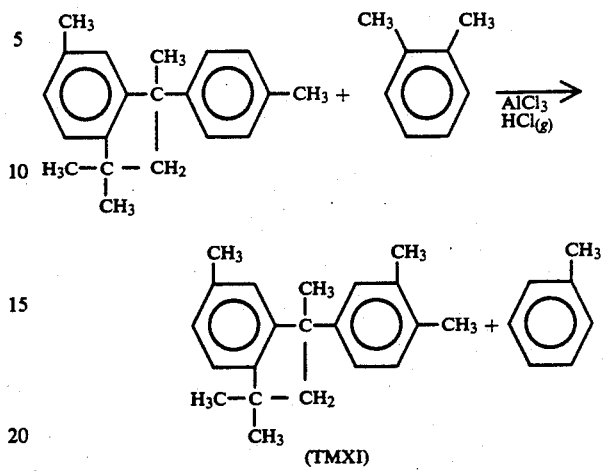

When TMXI is subsequently oxidized and then dehydrated, the corresponding mixed acid anhydride is formed:

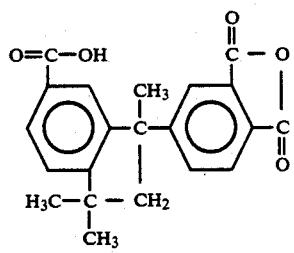

The alpha methyl styrene dimerization reaction to produce a starting 1,3,3,6-tetramethyl-1-aryl indan and the transaralkylation reaction to produce the transaralkylated product (preferably 1,3,3,6-tetramethyl-1-o-xylyl indan) are conveniently and preferably carried out in the same reactor. Also, the same solvent (preferably o-xylene) can be used in both reactions.

2,2-Di(Aryl)Propanes from Alpha Methyl Styrenes

In a related aspect, the present invention provides a new and very useful three successive step method for the production of 2,2-di(alkyl-substituted)aryl propanes from alpha methyl styrenes, as follows:

Step (1): Hydrochlorination of alpha-methyl styrene or of a lower alkyl ring substituted alpha-methyl styrene, to form a 2-phenyl-2-chloropropane (PCP).

Step (2): Alkylation (or coupling) of a methyl-substituted benzene, such as toluene or o-xylene, with such PCP in the presence of both a catalytically effective amount of a Friedel-Crafts catalyst, and also a molar excess of such methyl-substituted benzene, to form the corresponding 2-phenyl-2-aryl propane (PAP).

Step (3): Transaralkylation of such PAP with such a methyl-substituted benzene, in the presence of both a catalytically effective amount of a Friedel-Crafts catalyst, and also a molar excess of such methyl-substituted benzene, to form a desired 2,2-di(methyl-substituted)phenyl propane (SPAP).

Steps (1), (2), and (3) are each preferably carried out under liquid phase conditions in the presence of the same methyl-substituted benzene which functions both as a solvent and a reactant. In general, such methyl-substituted benzene is selected to have a different methyl substitution from the lower alkyl substitution present on the phenyl nucleus of the starting alpha methyl styrene.

The Friedel-Crafts catalyst of step (2) preferably comprises an adduct of aluminum chloride and nitromethane wherein the molar ratio of aluminum chloride to nitromethane ranges from about 0.25:1 to about 2:1, and wherein the mole ratio of aluminum chloride to nitromethane is more preferably about 1:2, while the Friedel-Crafts catalyst of step (3) preferably comprises an adduct of aluminum chloride and hydrogen chloride wherein the mole ratio of aluminum chloride to hydrogen chloride ranges from about 5:1 to about 0.5:1, and more preferably is about 1:1.

This three-step process is now illustrated for present descriptive and illustrative purposes by a presently preferred embodiment of this process wherein such steps are constituted as follows:

Step (1): Hydrochlorination of alpha-methyl styrene with hydrogen chloride to form 2-phenyl-2-chloropropane (PCP).

Step (2): Alkylation (or coupling) of o-xylene with PCP in the presence of a molar excess of said o-xylene and in the presence of a catalytically effective amount of a catalyst comprised of such adduct of aluminum chloride and nitromethane to form 2-phenyl-2-xylylpropane (also known as 2-phenyl-2-(3'4'-dimethyl)-phenyl propane (PXP)).

Step (3): Transaralkylation of PXP in the presence of a molar excess of o-xylene and in the presence of a catalytically effective amount of a catalyst comprised of such adduct of aluminum chloride and hydrogen chloride to form 2,2-dixylyl propane (also known as 2,2-di(3',4'-dimethyl)phenyl propane (DXP)).

In general, the step (1) hydrochlorination can be carried out by any convenient procedure. However, it is presently preferred to accomplish hydrochlorination by first dissolving the starting alpha methyl styrene in the methyl-substituted benzene (for example, in the above preferred embodiment, in o-xylene) and then bubbling hydrogen chloride gas through this solution while maintaining a temperature which is below about 10° C. (50° F.), and more preferably below about 0° C. (32° F.). The low temperature of reaction is required since the reaction is reversible. Excess HCl can be discharged to a scrubber.

The presence of unreacted or reformed alpha methyl styrene is undesirable since acid catalyzed dimerization can occur with formation of 1,3,3-trimethyl-1-phenyl indan. Therefore, the starting alpha methyl styrene is preferably substantially completely hydrochlorinated. The yields are substantially quantitative.

The step (2) preferred alkylation of o-xylene by PCP can be carried out by any convenient specific procedure. However, as indicated, it is presently preferred to accomplish such alkylation under liquid phase conditions in the presence of a catalytically effective amount of a Friedel Crafts (Lewis acid) alkylation catalyst comprised of an adduct of aluminum trichloride and nitromethane wherein the mole ratio of aluminum trichloride to nitromethane is about 1:2. The adduct moderates catalyst activity and affords a relatively higher selectivity to PXP.

Procedurally, various techniques can be used. In a present preference, the 2-phenyl-2-chloropropane (PCP) is dissolved in a molar excess of the methyl-substituted benzene (for the preferred example, o-xylene) and the temperature of the resulting PCP or first solution is maintained below about 10° C. (50° F.) and preferably below about 0° C. (32° F.). To such a PCP solution is added with mixing a measured amount of a separately prepared second solution of the catalyst in the same solvent medium (a methyl-substituted benzene) which for the preferred example is o-xylene. Preferably, the amount of such a catalyst solution so admixed is just sufficient to initiate the alkylation reaction (as marked by HCl evolution). Conveniently, the concentration of $AlCl_3$ in such second solution is in the range of about 0.1 to about 2 weight percent based on total second solution weight. Additionally, such second solution also contains the nitromethane in an amount sufficient to achieve a mole ratio of $AlCl_3$ to $CH_3NO_2$ which is within the range above indicated. Thus, the quantity of catalyst in the combined first and second solutions is, in general, sufficient to produce in such combined first and second solutions a catalyst concentration which initiates and maintains the desired alkylation reaction. A suitable and presently preferred starting mole percent of catalyst based on PCP is in the range of about 0.25 to about 5 mole percent in the combined solutions. The alkylation is accompanied by evolution of an equivalent amount of HCl from the reaction system. Evolved HCl can be discharged to a scrubber.

The alkylation is characteristically carried out at relatively low temperatures (preferably below about 10° C. (50° F.) to minimize competitive dehydrochlorination of PCP and formation of 1,3,3-trimethyl-1-phenyl indan.

The alkylation can be practiced batchwise (preferred) or continuously. One can employ a starting mole ratio of o-xylene to PCP of about 5:1 to 50:1 with a present preference being in the range from about 10:1 to 30:1.

When, as above indicated, such $AlCl_3 \cdot CH_3NO_2$ catalyst adduct concentration in the combined cooled solution reaches an effective level, HCl outgasing spontaneously occurs. HCl evolution and PXP formation are usually substantially complete within a few minutes. The temperature of the combined solution during the reaction period is preferably maintained below about 10° C. (50° F.). The reactant solution is cooled as needed during the reaction period to control the relatively rapid exotherm.

When this reaction is carried out on a relatively small scale, such as with a reacting liquid phase containing less than about 1 mole of PCP, the rapid HCl evolution is of no particular concern and is easily handled, for example, by passing the evolved HCl gas into a sodium hydroxide bath (which acts as a scrubber). However, when carried out on a relatively larger scale, the copious amount of evolved HCl gas (22.41 liters HCl per mole PCP) can become a major processing problem.

To circumvent and overcome this HCl evolution problem, and also to achieve maximized yields of PCP with minimal by-product production, a continuous process has now been discovered wherein the 2-phenyl-2-chloropropane (PCP) and the aluminum trichloride/nitromethane adduct catalyst are continuously admixed together as solutes in the methyl-substituted benzene as solvent (preferably, as solutes in o-xylene) under liquid phase conditions. Particularly when this continuous process is practiced using the preferred operating conditions taught hereinbelow, the product PXP is produced in high yield with minimal by-products, and also the HCl evolution is controlled.

The rate at which the PCP is admixed with the adduct catalyst in this continuous process is such that both (a) the evolution of the hydrogen chloride gas from the resulting mixture occurs at a predetermined and generally uniform rate, and (b) the reaction exotherm does not generate heat at a rate sufficient to cause the reactant mixture temperature to rise above a predetermined value. The reaction mixture is preferably maintained at a temperature in the range of about 0° to about 20° C. (32° to 68° F.). External cooling can be used, if needed or desired, until HCl gaseous evolution ceases.

In such a continuous process, a first feedstream is introduced at a regulated continuous rate from a feed source while concurrently a second feedstream is introduced at a regulated continuous rate from a suitable source. The first feedstream and the second feedstream are vigorously and continuously stirred in the reactor by an agitator, or like means.

Referring to FIG. 1, the first feedstream 11 conveniently comprises, on a 100 weight percent total weight basis, a solution of about 7 to 37 weight percent PCP dissolved in, correspondingly, about 63 to 93 weight percent of the methyl-substituted benzene (preferably o-xylene). The second feedstream, 13, conveniently comprises on a 100 weight percent total weight basis, a solution of (a) about 0.1 to 1 weight percent aluminum chloride, (b) sufficient nitromethane to produce a mole ratio of aluminum chloride to nitromethane of about 1:2, and (c) about 99 to 99.9 weight percent of such methyl-substituted benzene (preferably o-xylene).

The pumping rate of the first feedstream relative to the pumping rate of the second feedstream into the reactor 10 is such that the mole ratio of PCP to Friedel-Crafts catalyst is in the range of about 10:1 to 250:1 at the time of first and second feedstream introduction into reactor 10. At the time of admixing, the temperature of the first feedstream is preferably below about 10° C. (50° F.) and more preferably is below about 0° C. (32° F.). The temperature of the second feedstream is ambient. The temperature of the admixed reactants in the reactor 10 is preferably maintained below about 10° C. (50° F.). Evolved HCl gas is continuously vented from an upper location in the reactor 10 through a conduit 20.

When the liquid level 17 in reactor 10 reaches a predetermined point, it overflows into a conduit 18 and passes into a quench tank 19. Alternatively, a pump (not shown) could be used to maintain a desired fluid level and to transport effluent into the quench tank 19. By regulating the respective feed rates of the first and the second feedstreams through respective feed conduits 21 and 22 into reactor 10, the residence time of reactants in reactor 10 is controlled, and is the upper temperature reached by the reactants in the reactor 10, as well as the HCl evolution rate. External cooling of reactor 10 is thus avoidable; however, if desired, the admixed reactant liquids in the reactor 10 can be cooled by external cooling means, such as a water cooled jacket or the like (not shown) around reactor 10. Conveniently and preferably, the reactants in the reactor 10 are contained therein for a time period sufficient to permit the alkylation reaction to become at least about 98 percent completed (based on conversion of starting PCP), preferably higher. A present preference is to use a reactant mixture holding period in reactor 10 which is less than about 1 minute and most preferably which is less than about 8 seconds.

By thus continuously bringing together the reactants and catalyst in reactor 10, the volume of HCl gas generated per unit of time is regulated at a level suited for the absorption and take-up capabilities of the particular, preferably conventional, HCl-receiving unit employed. For example, such unit can comprise a conventional scrubber 23 of the type wherein HCl gas from reactor 10 is received through conduit 20 and is passed upwardly and countercurrently through scrubber 23 against a downwardly descending stream of liquid, such as an aqueous solution of sodium hydroxide, or the like (not detailed).

The liquid effluent from reactor 10 contains the produced PXP in methyl-substituted benzene solution along with entrained HCl gas bubbles. The liquid surface in reactor 10 is a location in the system where the HCl gas content admixed with liquid is maximal. This effluent comprises liquid and HCl gas (in the form of bubbles), and such is conveyed through conduit 18 into quench tank or zone 19 wherein such effluent is discharged, and admixed with, a preexisting water bath 24 in quench tank 19 which is vigorously agitated by an agitator 26, or the like. The liquid effluent from reactor 10 is substantially insoluble in water. However, the water bath provides a convenient heat sink for the liquid effluent. The volume of water is preferably chosen so that the temperature of the admixture in the quench tank 19 is maintained below about 50° C. (122° F.), without auxiliary cooling means. The quench tank 19, however, can be provided, if desired, with external cooling means, such as tank jacketing, or the like (not shown). The size of the quench tank is preferably such that liquid effluent received therein from the mixing zone can be not only quenched and collected therein but also held for a period of time. When a desired quench tank fill level is reached, another quench tank (not shown) can be, if desired, provided to receive the reactor 10 effluent. The quench tank 19 is provided with an upper vent conduit 28 from which evolved HCl gas is removed for scrubbing.

After HCl evolution from the liquid in the quench tank 19 has ceased, and heat is no longer evolved, quench tank 19 agitation is terminated. Separate organic and water liquid layers are allowed to form in the quench tank 19, thereby permitting a solution, such as one comprised of PXP in o-xylene, to be separated.

This PXP product solution is suitable for direct usage in the next step (transaralkylation) without further processing, but preferably is dried. For example, such a solution preferably comprises on a 100 weight percent basis about 7 to about 37 weight percent PXP, about 0 to about 2 weight percent unreacted PCP, and about 63 to about 93 weight percent o-xylene. The residual PCP present in such solution does not adversely affect the subsequent transaralkylation reaction nor otherwise offset the quality of the DXP recovered from the transaralkylation reaction.

At the end of the alkylation reaction, whether practiced batchwise or continuously, the AlCl$_3$ is removed by using any convenient Friedel-Crafts catalyst separation procedure, such as complex formation or by separation of the denser red oil phase containing the AlCl$_3$. It is presently preferred to remove the AlCl$_3$ by quenching the liquid reaction product with water which is preferably basic. To avoid exotherm, as is desired, the water quench can be preceded by first quenching the reaction product with methanol or the like. These quenching operations can be practiced with mechanical agitation followed by separation. A convenient weight ratio of water to liquid reaction product is in the range of about 0.5:1 to about 1:1. Quench times can vary. Convenient quench times range from about 1 to about 5 minutes for each of the methanol and water quenches. Preferably, quenching is promptly carried out at the end of the alkylation reaction to avoid or to minimize any product yield degradation of PXP such as can occur if the $AlCl_3$ is allowed to remain in contact with the liquid reaction product for an extended period of time. Also, in a preferred procedure, the red oil catalyst layer should be separated from the reaction mixture and quenched separately. This avoids product degradation due to the large exotherm produced during the catalyst quench.

While the nitromethane can be separated from the liquid reaction product by subjecting the liquid reaction product to drying, as in a conventional, so-called "rotovap", or the like, no clear process advantage has as yet been established or demonstrated favoring removal of nitromethane before the next step (transaralkylation).

There is a possibility that some residual moisture can be present in the liquid reaction product. Such can be removed by distilling the liquid reaction product to separate therefrom unreacted methyl-substituted benzene, which also removes nitromethane and residual water, or by subjecting the liquid reaction product to drying, as in a "rotovap", or the like. If used, the drying can simultaneously remove both water and nitromethane.

The low boiling constituents present (that is, those which boil at a lower temperature than PXP, such as PCP, water, nitromethane, and possible by-products) may be removed from alkylation liquid reaction products before transaralkylation is undertaken to enhance and to maximize DXP yields during and after transaralkylation is carried out. However, no clear process advantage has yet been established or demonstrated favoring removal of such low boiling agents except water, of course.

To avoid and to minimize loss of PXP, it is preferred to commence transaralkylation as soon as practical after completion of the alkylation reaction and the quenching and separation of the $AlCl_3$. The next step (3), transaralkylation, wherein the phenyl group in PXP is exchanged by methyl-substituted benzene to produce DXP, is conveniently carried out by introducing the product of the alkylation, that is, the step (2) product as above characterized, directly into a desired reaction zone. Additional such methyl-substituted benzene can be added to achieve a desired dilution for the PXP in such methyl-substituted benzene, such as a mole ratio of o-xylene to PXP in a preferred range of 10:1 to 30:1. The transaralkylation conditions employed are as above described. Thus, a product PAP solution in such methyl-substituted benzene, such as results from alkylation, is conveniently and preferably directly charged into a transaralkylation reaction zone along with a catalytically effective amount of the Friedel-Crafts catalyst.

The Friedel-Crafts transformation catalyst preferably is aluminum trichloride in combination with hydrogen chloride preferably in about a 1:1 mole ratio. Any convenient or desired technique for introducing the catalyst into the liquid mixture to be here transaralkylated can be employed. For example, in one preferred procedure, the transaralkylation catalyst solution is preliminarily prepared. The catalyst solution comprises, on a 100 weight percent basis, about 1 to about 4 weight percent of such dissolved aluminum chloride, sufficient dissolved HCl to provide a mole ratio of HCl to aluminum chloride of about 1:1, the balance up to 100 weight percent thereof being aromatic liquid. Such solution is admixed with the solution of PXP in methyl-substituted benzene.

In one presently preferred procedure, HCl gas is first bubbled (e.g., sparged) into the PXP solution until such solution is saturated with HCl. Thereafter, particulate $AlCl_3$ is introduced, preferably rapidly and with vigorous mixing, into the resulting liquid system. The amount of $AlCl_3$ so added is within the range above indicated, and preferably is about 20 mole percent, based on PXP present in the solution.

It is also presently preferred to continue introducing HCl gas into the solution after $AlCl_3$ introduction preferably at an HCl addition rate which is sufficient to maintain an HCl saturation of the reactant liquid medium because such a continuing introduction seems to favor production of higher yields of the desired DXP product.

After $AlCl_3$ introduction and commencement of the transaralkylation, the reaction system is preferably continuously stirred for the duration of this step.

Upon admixture of such catalyst with such PAP solution (preferably, PXP solution in o-xylene), transaralkylation occurs under liquid phase conditions at room temperature.

A maximized yield of DXP appears to be achieved after a time interval in the range of about 2 to about 6 hours, although longer and shorter transaralkylation reaction times can be used if desired.

If additional dissolved $AlCl_3$ is introduced into the transaralkylating reaction mass during the progress of the reaction, an increase in yield of DXP has sometimes been observed for reasons which are not clear.

The product of such transaralkylation reaction preferably comprises, on a 100 weight percent total basis, about 10 to about 20 weight percent DXP, about 5 to about 10 weight percent PXP, about 5 to about 20 weight percent of various by-products, and about 50 to about 80 weight percent o-xylene. The yield of DXP is typically in the range of about 35 to about 45 percent (based on starting PXP).

At the end of this transaralkylation step or reaction, the $AlCl_3$ is removed from the liquid reaction product conveniently in a manner similar to that employed and above described herein in reference to the liquid reaction product of the PCP alkylation step or reaction, preferably using a water quench, and preferably interposing a methanol quench before the water quench. It is also preferred to remove the $AlCl_3$ promptly to avoid loss in yield of DXP through degradation.

A liquid reaction product, such as a DXP product, is preferably subjected to separation procedures to isolate the desired product, such as hereinbelow described.

Because of heat exposure considerations, and particularly if a batch distillation procedure is to be used, it is preferred to remove from the $AlCl_3$ quenched liquid reaction product as much chlorine or chloride compounds as possible prior to distillation to prevent and to minimize formation of indans and/or heavy by-products. Such removal is conveniently accomplished by washing the quenched reaction product with water.

One convenient procedure is to wash a quenched reaction product with from about 5 to 15 parts by weight of water (preferably demineralized) per part of quenched reaction product for 30 to 60 minutes at 80° to 100° C. (176° to 212° F.). Such a wash can be accomplished batchwise by stirring a mixture of such reaction product in a reactor vessel, or the like.

Initially, the chlorine level of the quenched DXP-containing reaction product is typically and exemplarily in the range of about 1000 to about 2000 ppm, and such a wash typically reduces the chlorine content thereof to a level which is in the range of about 5 to 10 percent of such initial level.

Separation Procedures for DXP

Any convenient separation procedure, or combination of procedures, can be employed. However, it is presently preferred to employ a combination of fractional distillation followed by crystallization as hereinbelow described.

Separation of a desired transaralkylated product from a liquid reaction product which has been quenched to remove AlCl₃ and washed to reduce chlorine content can be accomplished using a fractional distillation tower, or the like, such as a column containing from about 5 to about 25 theoretical stages, although a column with more or less theoretical stages could be used, if desired.

In separation by distillation, the quenched and scrubbed transaralkylated reaction product containing DXP is transferred to a distillation column where the light material is first removed. For example, o-xylene is removed at 100 mm Hg and 15° F. (66° C.). Then, the pressure is preferably reduced, for example, to a value in the range of about 20 to 40 mm Hg, and the mixture fractionated at a reflux ratio in the range from about 2:1 to 20:1. For example, in the case of a DXP containing system, after o-xylene removal as above indicated, the pressure can be reduced to about 25 mm Hg and the resulting mixture fractionated at about a 5:1 reflux ratio to remove most of the PXP.

The residual material comprises mainly the desired product produced in the transaralkylation reaction. Thus, in the present illustration, the residue material comprises from about 85 to about 90 weight percent DXP. Fractionation of this material at reduced pressures similar to those above indicated and at elevated temperatures using a higher reflux ratio, such as a reflux ratio of from about 5:1 to 15:1, can be expected to yield cuts of above about 97 weight percent pure of desired product. For example, in the case of the DXP remaining material, fractionation at about 25 mm Hg and a 10:1 reflux ratio yielded several cuts each 98 to 99 weight percent pure DXP. Cuts having a lower purity of DXP are also additionally obtained.

When, for example, a recovered product needs to have a purity of greater than 98 weight percent for use in subsequent oxidation or the like, yet has a purity of less than this value, a further crystallization process may be employed to upgrade such below-grade distillation cuts to at least the minimum acceptable grade level. For example, in the case of a DXP product which is to be subsequently oxidized in an acetic acid solvent, acetic acid is usable as the solvent for crystallization. A below grade, but DXP-rich, cut, such as separated by a distillation as above described, is dissolved in excess concentrated acetic acid (such as 95 percent acetic acid) and is heated to a temperature of about 170° to about 200° F. (77° to 93° C.) with stirring. With stirring being continued, the resulting solution is cooled to about 32° F. (0° C.) where DXP crystals precipitate out after about five minutes while the temperature sharply rises to about 45° F. (7.2° C.). Stirring is preferably continued for from about 5 to about 15 minutes, after which the resulting slurry is filtered or centrifuged and the recovered crystals dried. Starting, for example, with about 88 weight percent pure DXP, a crystallized product purity of over 99 weight percent at about 90 percent yield is recoverable.

1,3,3-Trimethyl-1-Aryl Indans from Alpha Methyl Styrene

In another related aspect, the present invention provides a new and very useful two-step method for the production of 1,3,3-trimethyl-1-aryl indans from alpha-methyl styrenes, as follows:

Step (1): Dimerization of alpha-methyl styrene, or of a lower alkyl ring substituted alpha-methyl styrene, in the presence of a catalytically effective amount of an acid catalyst to form a 1,3,3trimethyl-1-phenyl indan (MPI).

Step (2) Transaralkylation of MPI with an alkyl-substituted aromatic compound, such as a methyl-substituted benzene, in the presence of both a catalytically effective amount of a Friedel-Crafts catalyst, and also a molar excess of such methyl-substituted benzene, to form a desired 1,3,3-trimethyl-1-(lower alkyl-substituted) phenyl indan.

Steps (1) and (2) are each preferably carried out under liquid phase conditions in the presence of the same methyl-substituted benzene. In general, such methyl-substituted benzene is selected to have a different methyl substitution from any lower alkyl substituents present on the phenyl nucleus of the starting alpha methyl styrene.

This two-step process is illustrated below.

Step (1): Dimerization of alpha-4-dimethyl styrene in the presence of a catalytically effective amount of an acid catalyst to form 1,3,3,6-tetramethyl-1-p-tolyl indan (TMTI).

Step (2): Transaralkylation of TMTI with a molar excess of o-xylene in the presence of a catalytically effective amount of a catalyst compound of an adduct of aluminum chloride and hydrogen chloride to form 1,3,3,6-tetramethyl-1-o-xylyl indan (TMXI).

In general, the step (1) dimerization is carried out by any convenient procedure. However, it is presently preferred to accomplish dimerization by first dissolving the starting alpha-methyl styrene in the methyl-substituted benzene and then bubbling hydrogen chloride gas through this solution maintained at about 0° C. (32° F.). However, a relatively higher temperature of about 50° C. to about 60° C. will expedite the dimerization reaction. The yield is substantially quantitative.

The next step (2), transaralkylation, is carried out by introducing the product of the dimerization, that is, the step (1) product, into a desired reaction zone. The transaralkylation conditions employed are as above described. Thus, if desired, a product MPI solution in methyl-substituted benzene, such as results from dimerization, is directly charged into a transaralkylation zone along with a catalytically effective amount of a Friedel-Crafts catalyst. An MPI solution, such as TMTI in o-xylene, is interveningly storable, if desired, but is chargeable directly to a reaction zone which already contains an added solution of the catalyst, e.g., an adduct of aluminum chloride with hydrogen chloride in about a 1:1 mole ratio.

Such a transaralkylation catalyst can be identical to the transaralkylation catalyst employed for producing DXP from PXP as described above. Such catalyst is conveniently prepared as above described.

Upon admixture of the MPI solution with the catalyst, transaralkylation occurs under liquid phase conditions at ambient conditions.

The yield of the desired MSPI is typically and preferably within range of about 30 to about 50 percent (based on starting MPI).

At the end of this transaralkylation step or reaction, the AlCl₃ is removed from the liquid reaction product in a manner similar to that employed and above described herein in reference to the liquid reaction product of the PCP alkylation step, preferably using a water quench, and preferably interposing a methanol quench before the water quench. Preferably, the AlCl₃ is promptly removed to avoid yield losses through degradation.

The liquid reaction product is preferably subjected to separation procedures to isolate the desired MSPI (preferably TMXI), such as hereinbelow described.

Because of heat exposure considerations, and particularly if a batch distillation procedure is to be used, it is preferred to remove from the AlCl₃ quenched liquid reaction product as much total chlorine as possible prior to distillation to prevent and to minimize formation of by-products, such as other unwanted indans, and the like. Removal of HCl and chlorine is conveniently accomplished by washing a quenched reaction product with water. For example, the wash procedure hereinabove described in reference to a DXP reaction product can be used and approximately equivalent reduction in chlorine content is achieved.

3,3',4,4'-Dixylylmethane

In a preferred process embodiment of the aromatic transformation process of this invention, a mixture of 2,2',3,3'-, 2,3',3,4'- and 3,3',4,4'-dixylylmethane isomers can be used to prepare 3,3',4,4'-dixylylmethane. In this particular reaction the isomeric mixture of dixylylmethanes can be converted to greater than 90 percent 3,3',4,4'-dixylylmethane. At this level of 3,3',4,4'-dixylylmethane in the product mixture, the 3,3',4,4'-dixylylmethane crystallizes readily and can be recovered by simple filtration.

Methods for preparing a mixture of 2,2',3,3'-, 2,3',3,4'- and 3,3',4,4'-dixylylmethane have been published. For example, Mironov et al., Zhurnal Prikladnoi Khimii 39:1614–1621 (1966), describes a method for preparing the mixture of dixylylmethanes by the condensation of o-xylene with formaldehyde catalyzed by toluenesulfonic acid, benzenesulfonic acid or sulfuric acid. In Farberov et al., Zhurnal Organicheskoi Khimii 4:163–168 (1968), the mixture of dixylmethanes formed by the condensation of o-xylene with formaldehyde catalyzed by an acid is described as a practically unresolvable mixture of isomers. In our analysis of the product mixture using a high performance gas chromatograph equipped with a capillary gas chromatographic column, we determined that the mixture comprises approximately 60 percent of the 3,3',4,4'-isomer, approximately 35 percent of the 2,3',3,4'-isomer and approximately 5 percent of the 2,2',3,3'-isomer. In order to isolate the desirable 3,3',4,4'-isomer from this reaction mixture after a standard washing procedure to remove the acid catalyst and a distillation procedure to remove light ends, unreacted o-xylene and heavy ends, one must cool the mixture to a low temperature of about −25° C. and the 3,3',4,4'-isomer crystallizes. The recovery, however, is poor. Typically only about 50 percent of the 3,3',4,4'-isomer is recovered.

However, upon treating the mixture of 3,3',4,4'-, 2,3',3,4'- and 2,2',3,3'-dixylylmethane isomers with o-xylene in the presence of a small amount of a Friedel-Crafts catalyst the transaralkylation process of this invention converts the mixture to predominantly 3,3',4,4'-dixylylmethane. Analysis by capillary gas chromatography indicates that the 3,3',4,4'-isomer is present in greater than 90 mole percent. The desired 3,3',4,4'-dixylylmethane isomer, after removing the excess o-xylene, crystallizes at room temperature, can be isolated in pure form by simple filtration and can be used for oxidation to benzophenone tetracarboxylic acid or for other uses.

The process temperature for this particular transaralkylation reaction is not critical; however, temperatures in the range of about −10° C. to about 60° C. are suitable, and a temperature of about 20° C. to about 30° C. is preferred. The ratio of o-xylene to the mixture of dixylylmethanes is important for acceptable conversion to the desired 3,3',4,4'-dixylylmethane isomer. Preferably, there should be at least one mole of o-xylene per mole of the dixylylmethane mixture. Less o-xylene may be used; however, better results are obtained when the mole ratio of o-xylene to the dixylylmethane mixture is greater than 1. The mole ratio of o-xylene to the mixture of dixylylmethane isomers can be about 0.1:1 to about 50:1, and preferably is about 1:1 to 10:1.

The level of Friedel-Crafts acid (Lewis Acid) catalyst is preferably in the range of about 20 mole percent to about 2 mole percent, based on the amount of the dixylylmethane mixture present. More preferably, the range of catalyst is about 5 mole percent to about 15 mole percent. Although aluminum chloride is a preferred Friedel-Crafts catalyst, other Friedel-Crafts catalysts are suitable. For example, aluminum bromide, zinc chloride, zinc bromide, and the like.

The reaction time is not a critical factor, although the reaction mixture must be allowed to reach a state where acceptable yields and conversion are attained. The reaction is conveniently followed by gas chromatographic analysis techniques.

Depending upon the catalyst present and the ratio of o-xylene to dixylylmethane isomers, the reaction is complete within about one minute to about one hour. The reaction pressure also is not critical factor. Atmospheric pressure is preferred, but the pressure can be lower or higher. Pressures in the range of from about 0.1 atmosphere to about 10 atmospheres are suitable.

Thus, the transaralkylation process of this invention is suitable for preparing relatively pure 3,3',4,4'-dixylylmethane by the process comprising: reacting in a suitable reaction zone a reaction mixture comprising o-xylene, a catalytically effective amount of a Friedel-Crafts catalyst and a dixylylmethane isomer selected from 2,2',3,3'-dixylylmethane 2,3',3,4'-dixylmethane and mixtures thereof, for a time sufficient to convert a substantial portion of said isomer to 3,3',4,4'-dixylylmethane product.

The 3,3',4,4'-dixylylmethane product is actually in a mixture of dixylylmethanes comprising mainly the desired 3,3',4,4'-dixylylmethane and lesser amounts of 2,2',3,3'- and 2,3',3,4'-dixylylmethanes. Preferably, 3,3',4,4'-dixylylmethane is greater than about 75%, more preferably greater than about 85% and most preferably greater than about 90% (by weight) of the mixture of dixylylmethanes produced.

In subsequent process steps, the so formed 3,3',4,4'-dixylylmethane product can be removed from the reaction mixture by conventional methods, preferably after first neutralizing and removing the Friedel-Crafts catalyst, preferably by an aqueous washing step. Water or water and methanol can be used to neutralize the Friedel-Crafts catalysts.

Preferably, after neutralizing and removing the Friedel-Crafts catalyst, any excess of o-xylene is removed, preferably by distillation, and the remaining product is distilled, preferably vacuum distilled, to remove light and heavy ends to produce a dixylylmethane mixture rich in 3,3',4,4'-dixylylmethane. This mixture rich in 3,3',4,4'-dixylylmethane typically crystallizes after standing at room temperature for 8-24 hours and pure 3,3',4,4'-dixylylmethane can be recovered by filtration or by other suitable means, e.g., centrifugation, for separating crystalline 3,3',4,4'-dixylylmethane from any remaining liquid materials.

EXAMPLES

The following examples illustrate this invention. These examples are not to be construed as limiting the scope thereof, however.

EXAMPLE 1

Formation of PCP from Alpha Methyl Styrene by Hydrochlorination

A solution of alpha-methyl styrene dissolved in o-xylene at a weight ratio of alpha-methyl styrene to o-xylene of about 1:5 was prepared and cooled to 0° C. (32° F.). Dry HCl gas was sparged through the chilled mixture. When conversion of the alpha-methyl styrene to 2-phenyl-2-chloro propane (PCP) was complete, no further absorption of HCl takes place in the reactor. By providing a gas bubbler on the outlet of the reactor, the presence of HCl at the bubbler was used as the technique for determining that conversion was complete. Since the reaction was exothermic, the rate of HCl addition during reaction was determined by the cooling capacity available, and by the desired operating temperature. Excess HCl was discharged into a scrubber.

EXAMPLE 2

Formation of PXP from PCP by Batch Alkylation

Immediately following the completion of the hydrochlorination reaction of Example 1, the alkylation of PCP was initiated by the addition of a catalytic amount of $AlCl_3$ to the reaction mixture with stirring (about 0.02 moles $AlCl_3$ per mole of PCP) which mixture was preliminarily cooled. The $AlCl_3$ was preliminarily slurried with some o-xylene to which was added an amount of nitromethane equal to twice the number of moles of $AlCl_3$. The $AlCl_3$ and the nitromethane were fully dissolved. This catalyst solution was then added to the PCP solution until reaction commenced. The mole ratio of solvent (o-xylene) to PCP was about 5:1. The resulting reactant mixture temperature was maintained at about 25° F. (−4° C.). The reactants were continuously agitated. A voluminous outgasing of HCl occurs spontaneously, and the HCl gas so evolved was delivered to a scrubber. The HCl gas evolution was substantially complete within about 5 minutes. The reaction product was found to comprise a solution of about 20 mole percent PXP in o-xylene. The conversion efficiency (yield) was found to be greater than 90 mole percent (based on starting PCP).

At the conclusion of this reaction, the $AlCl_3$ was quenched first with methanol and then was extracted with several water washes. Quenching first with water was found to be extremely exothermic and difficult to control. Preliminary quenching with methanol followed by water quenching avoided an excessive exotherm.

By adding only enough $AlCl_3$ to initiate this reaction (which was then very rapid and self-sustaining), PXP yields were obtained which are above about 85-90 mole percent (based on PCP). This catalyst addition procedure is also advantageous because it compensates for any variation in the activity of the $AlCl_3$ (possibly due to moisture absorption or the like). Further, no vacuum was created. The product is usually dried to remove traces of water which can have an adverse effect on $AlCl_3$ in a subsequent process step.

EXAMPLE 3

Formation of PXP from PCP by Continuous Alkylation

The present continuous alkylation process utilized an embodiment of the apparatus hereinabove described and shown in accompanying FIG. 1.

The first feedstream comprised a solution of 10 moles of PCP dissolved in 50 moles of o-xylene, such PCP having been prepared by the process of Example 1, and such solution being adjusted with added o-xylene to achieve the o-xylene/PCP mole ratio of about 5:1 to about 10:1.

The second feedstream comprised 440 ml of o-xylene having dissolved therein 13.2 gm (0.10 moles) $AlCl_3$ and 11.2 gm (0.18 mole) nitromethane. This solution was prepared by adding the $AlCl_3$ to o-xylene, with the $AlCl_3$ being in a particulate form, followed by addition of nitromethane with stirring until solution was achieved.

The first feedstream was pumped at the rate of 450 ml per minute into the mixing zone, and the second feedstream was simultaneously pumped into the mixing zone at the rate of 30 ml per minute. Foaming and a vortex were induced in the mixing zone by concurrent rapid stirring. At the time of mixing, the first feedstream was maintained at a temperature not greater than about 25° F. (−4° C.), while the second feedstream was maintained at ambient temperature (about 72° F. (22.° C.).

The average holding capacity of the mixing zone was approximately 330 ml, and the average residence time in the mixing zone was about 40 seconds. The temperature of the reaction mass in the mixing zone was in the range of about −5° to about +5° C. (about 23° to about 41° F.) without external cooling being employed. The overflow of reaction product from the top surface of the reaction mass passed through a conduit from the mixing zone into a quench tank. The quench tank was preliminarily charged with 500 ml of water. The mixture formed in the quench tank was rapidly and continuously agitated by a mechanical stirrer.

Vented HCl gas from both the mixing zone and the quench tank was delivered to a common scrubber. The size of the quench tank was sufficient to contain the entire product effluent from the mixing zone. The temperature of the quench tank was maintained at all times below about 40° C. (about 104° F.).

After evolution of HCl gas had ceased in the quench tank, quench tank agitation was terminated, and separate aqueous and non-aqueous liquid phases were permitted to form. Thereafter, the non-aqueous phase was separated and was found to comprise a solution of about 16 mole percent PXP, about <1 mole percent PCP, and about 84 mole percent o-xylene. The conversion of PCP to PXP was thus greater than about 95 percent (based upon starting PCP).

EXAMPLE 4

Formation of PXP from PCP by Continuous Alkylation

The procedure of Example 3 was repeated except that the rate at which the first feedstream and the rate at which the second feedstream were each respectively charged to the mixing zone was increased proportionately so that the average residence time of the admixed reactants in the mixing zone was approximately 4 seconds. The rate for the first feedstream was about 110-120 milliliters per second and for the second about 7 milliliters per second. Examination of the non-aqueous product recovered from the quench tank shows that the overall selectivity of the process to produce PXP from PCP was not less than about 90 percent. The product solution comprised about 16 mole percent PXP, about <1 mole percent PCP, and about 84 mole percent o-xylene. The conversion efficiency to PXP was thus about 90-95 percent (based on starting PCP).

The high selectivity and yield was achieved while the rate of HCl solution was controlled, foaming was controlled, and heat of reaction was controlled.

EXAMPLE 5

Transaralkylation of PXP to DXP

Run (a) To the catalyst quenched PXP solution in o-xylene produced by the process of Example 4 above which contained about 95 mole percent PXP was added sufficient additional o-xylene to produce a 20-fold molar excess of o-xylene relative to PXP.

Optionally, all of the o-xylene from the PXP mixture produced in Example 4 can be stripped off prior to diluting to 20:1 with added o-xylene in order to enhance yields of DXP in the transaralkylation. In this example, the starting mixture from the alkylation procedure was not preliminarily stripped to separate o-xylene.

The resulting solution was saturated with HCl by sparging in dry HCl gas, after which 0.2 molar equivalent of the AlCl$_3$ (based on starting PXP) was added quickly with mixing as a particulate solid. No noticeable heat evolution was observed.

The resulting liquid mixture was agitated and the reaction to form DXP was carried out at room temperature and was not noticeably exothermic. The resulting solution was maintained at room temperature for several hours.

The product was quenched by the procedure described in Example 2.

Thereafter, an analysis of the resulting solution revealed a distribution of DXP and PXP in a gas chromatogram area percent ratio of 30/55 which corresponds to a composition of about 3 mole percent DXP, about 5 mole percent PXP, and about 90 mole percent o-xylene. Identity of the PXP and of the DXP was established by mass spectrometer. The yield of DXP was about 30 area percent as shown by a product chromatogram on an o-xylene free basis.

Run (b) The foregoing procedure was repeated a second time using a starting mixture containing an identical amount of PXP (96 percent); however, on an o-xylene free basis, the chromatogram of the quenched product showed a DXP yield of 47.8 area percent.

A possible explanation for the observed yield difference between run (a) above and the present run (b) was that the PXP mixtures for the two runs contained different amounts of water.

In the case of the second run, after about 6 hours, an additional 30 grams (25 mole percent based on o-xylene) of o-xylene was added with stirring to the reaction mixture. A slight increase in DXP yield resulted initially. However, after two days of continuous stirring at ambient temperatures, the unquenched mixture contained only 27.7 area ratio DXP showing that extensive product decomposition occurred.

Run (c) In another run, the foregoing procedure of the first run (Run (a)) was repeated except that the amount of AlCl$_3$ added initially was increased by 50 percent. However, on an o-xylene free basis, the chromatogram of the quenched product showed a slightly reduced DXP formation.

After about 5 hours, HCl addition was resumed for one hour. The DXP area percent (measured in same manner) increased to 54.6. This indicates that maintaining an HCl saturated solution throughout the course of a transaralkylation reaction was beneficial in increasing DXP yield and in decreasing reaction time.

Run (d) In another run, the foregoing procedure of the first run (Run (a)) was again repeated except that no HCl was used. Examination of the product mixture showed that a greatly reduced area percent of DXP resulted (identically measured).

Run (e) In another run, the foregoing procedure of the first run (Run (a)) was again repeated except that initially all o-xylene was removed by stripping after which the residue was diluted with fresh o-xylene in an amount sufficient to achieve a weight ratio of o-xylene to PXP of 10:1. Examination of the product mixture showed that the DXP area ratio dropped somewhat, but was still 43 area percent (measured as above). This was an acceptable yield.

Run (f) To evaluate process reproducibility, a starting PXP feed solution containing 97.7 percent of PXP was first prepared by the procedure of Example 2, above, and then was dried in a "rotovap" to remove residual water and nitromethane. The resulting feed solution was then processed using the procedure of the first run (Run (a) above). The results are shown in Table I below.

TABLE I

| Transaralkylation DXP Reproducibility | | | |
|---|---|---|---|
| | Yields (Area Percent of Product) | | |
| Run | DXP | PXP | Total |
| A | 44.1 | 34.5 | 78.6 |
| B | 43.8 | 32.8 | 76.6 |
| C | 47.7 | 31.0 | 78.7 |

These results illustrate the reproducibility of the transaralkylation process.

Run (g) To further evaluate process reproducibility, a starting PXP feed solution prepared by the process of Example 2 above, and containing 96.4 percent PXP was similarly processed by the procedure of run (a). No preliminary drying was carried out. Comparable results to those obtained above described in run (f) were obtained (47.8 area percent DXP, 29.2 area percent PXP, and 77.0 area percent total). This illustrates that drying to remove water and nitromethane was probably not necessary in order to maximize yields of DXP.

Run (h) The procedure of run (a) was repeated using an undried starting PXP feed solution prepared by the process of Example 2 above and containing only 91.9 percent PXP, and comparable results to those observed in run (g) were obtained (48.5 area percent DXP, 31.7 area percent PXP, and 80.2 area percent total) indicating process flexibility.

Run (i) Another run with an undistilled and undried starting PXP feed solution containing 93.5 percent PXP was carried out using the procedure of the first run (above) except that half the amount of AlCl$_3$ (0.1 mole AlCl$_3$ based on PXP) was used. Comparable results were obtained (41.7 area percent DXP, 34.9 area percent PXP, and 76.6 area percent total).

Run (j) Another run with an undistilled and undried starting PXP feed solution containing 96.0 percent PXP was carried out using the procedure of the first run (run (a)) procedure except the quantity of o-xylene present was halved to produce an o-xylene weight ratio to PXP of 5:1. The results revealed that the amount of DXP produced was substantially reduced (35.8 area percent DXP, 26.9 area percent PXP and 62.7 area percent total).

Run (k) Another run with an undistilled and undried starting PXP feed solution containing 94.1 percent PXP was carried out using the first run procedure (run (a)) except that the AlCl$_3$ was added with the reactant solution being maintained at 45° F. (7° C.) after which the resulting reactant solution was warmed to room temperature for the rewarming run time. The results were comparable (48.7 area percent DXP, 25.6 area percent PXP, and 74.3 area percent total).

Run (l) Another run similar to the procedure of the run (a) (above) was carried out, but using the alkylated product of Example 3 as a starting material. The product obtained is comparable to that obtained in run (a) above.

In general, when a reaction product mixture is heated, the formation of heavy by-products is accelerated.

EXAMPLE 6

Preparation of 2-Phenyl-2-Chloro Propane (PCP)

The procedure of Example 1 was repeated except that toluene replaced o-xylene. PCP was obtained in a yield similar to that obtained for phenylchloropropane, but in a toluene solution.

EXAMPLE 7

Preparation of 2-Phenyl-2-Tolyl Propane by Continuous Alkylation

The procedure of Example 4 was repeated using the PCP solution of Example 6 and also using added toluene to obtain a starting solution containing 10 moles of PCP and 50 moles of toluene.

EXAMPLE 8

Transaralkylation of 2-Phenyl-2-Tolyl Propane to Produce 2,2-Tolylpropane

The procedure of Example 5(a) above was repeated except that the product solution of Example 7 replaced the starting solution of Example 4. To such starting solution additional toluene was added to produce a 20-fold molar excess of toluene relative to 2-phenyl-2-tolyl propane.

After several hours, an equilibrium distribution of 2-phenyl-2-tolyl propane and 2,2-ditolyl propane DTP in a gas chromatograph area percent ratio of 12/53 was obtained. The yields were similar to those for DXP, i.e., about 40 mole percent. The composition consisted of a mixture of 2-phenyl-2-tolyl propanes, substituted isomers of DTP, and the corresponding tolyindans (about 20-30 mole percent).

The 2-phenyl-2 tolyl propane thus prepared by the AlCl$_3$ catalyzed continuous alkylation procedure described in Example 7 was a mixture of two or possibly three isomers: mono-para, mono-meta, and perhaps mono-ortho in an approximate ratio of 60:1:1. The transaralkylation procedure of the present example not only produces ditolyl propanes, but also produces an altered distribution of the remaining 2-phenyl-2-tolyl propanes. The mono-meta isomer increases dramatically in concentration to an extent that the ratio of meta to para isomers increased from 1:60 to 2:1.

Three ditolyl propanes were formed during the present transaralkylation: meta-para, meta-meta, and para-para. Their respective ratios were about 1:1:0.24. The complexity of the product profile was believed to be a result of rapid intra-molecular isomerization of reactants and products. This product profile was more complex than that observed for similar reactions involving transaralkylation of 2-phenyl-2-xylyl propane with excess o-xylene (see, for instance, Example 5).

The products can be separated by fractional distillation to produce yields of meta-para and meta-meta isomers which are each oxidizable to the corresponding carboxyl-substituted derivatives. Without fractional distillation, the product isomer mixture can be oxidized to produce mixed isopropylidenebisbenzoic acids which are suitable as a feedstock for polymer formation reactions.

EXAMPLE 9

Preparation of 3,3',4,4'-Dixylylmethane from Mixed Dixylylmethanes

A 500 ml, 3-neck round bottom flask was equipped with a mechanical stirrer, thermometer, nitrogen purge tube and a pressure equalizing dropping funnel. The flask was charged with o-xylene (200 ml, 1.64 moles) and toluene sulfonic acid (8.4 g, 0.045 moles) and this mixture was heated to 100° C. A solution of trioxane (11.25 g, 0.38 moles) dissolved in o-xylene (95 ml, 0.78 moles) was added to the reaction mixture through the dropping funnel over a one hour period. After the complete addition of the trioxane solution, the dropping funnel was replaced with a reflux condenser fixed to a Barrett trap. The temperature of the reaction mixture was increased to 100°-125° C. and held there for approximately 4 hours during which time water collected in the Barrett trap. At this stage, the reaction mixture contained a mixture of dixylylmethane isomers in the following approximate relative amounts: 3,3',4,4'-(65%), 2,3',3,4'-(30%) and 2,2',3,3'-(5%). (Although this mixture was not isolated, similarly prepared and isolated mixtures of dixylylmethane isomers are liquid at room temperature). The reaction mixture was cooled to room temperature and 5.0 g of anhydrous aluminum chloride were added in two portions over a one hour period and the mixture stirred for one hour. The reaction mixture was then quenched by slowly adding 75 ml of methanol followed by 75 ml of water. Hexadecane (10.01 g) was added as an internal standard for gas chromatographic analysis.

The reaction product mixture was analyzed by gas chromatography using a 50 meter by 0.25 mm Superox (Carbowax 20M) capillary column (100° C. initial for 4 minutes then 16° C./minute to 230° C.). The yield of dixylylmethanes was 64% based on the amount of formaldehyde added. The ratio of 3,3',4,4'-dixylylmethanes to 2,3',3,4'-dixylymethane was 90.2%:7.76%. The 2,2',3,3'-Isomer, together with unknowns, totaled 2.04%.

EXAMPLE 10

Preparation of 3,3',4,4'-Dixylylmethane from Mixed Dixylylmethanes

In the same apparatus as described in Example 9, the reaction flask was charged with o-xylene (295 ml, 2.42 moles) and sulfuric acid (20.4 g of 96.2% sulfuric acid, 0.20 moles). This stirred mixture was heated to 105°–110° C. and held there while a formaldehyde solution (30.4 g of 37 wt. %, 0.38 moles) was added over a 45 minute addition period. During this time, water collected in the Barrett trap. This reaction mixture was then heated to 120° C. to remove residual water. The reaction mixture at this stage, similar to the reaction mixture obtained in Example 9, contained a mixture of dixylylmethane isomers in the following approximate relative amounts: 3,3',4,4'-(65%), 2,3',3,4'-(30%), 2,2',3,3'-(5%). Aluminum chloride (5 g) was added in the same manner as described in Example 9, and the resulting reaction mixture analyzed as described in Example 9. The yield of dixylylmethane was 57.8% based on formaldehyde added. The ratio of 3,3',4,4'-dixylylmethane to 2,3',3,4'-dixylylmethane was 78.7% to 12.5%. The remaining products consisted of unknowns and the 2,2',3,3'-isomer.

The lower ratio of 3,3',4,4'- to 2,3',3,4'-dixylymethane produced in this Example relative to Example 9 is believed to be due to the excessive amount of sulfuric acid catalyst used (0.8 moles of $H_2SO_4$ per mole of o-xylene, whereas in Example 9, 0.2 moles of toluene sulfonic acid were used per mole of o-xylene). The excess sulfuric acid may have deactivated the aluminum chloride or altered its catalytic function.

EXAMPLE 11

Large-Scale Preparation of 3,3',4,4'-Dixylylmethane

A 12 liter, 3-neck round-bottomed flask was equipped with a stirrer, a condenser attached to a Barrett trap, a nitrogen sparge tube and a thermometer. The flask was charged with o-xylene (8260 ml, 67.7 moles) and sulfuric acid (571 g, 5.6 moles). This mixture was heated to 115° C. with stirring. Formaldehyde solution (811 g of 37%, 10.0 moles) was slowly added to the reaction mixture through the pressure equalizing dropping funnel over a 2–3 hour period. After cooling to room temperature, the total reaction mixture was transferred to a separatory funnel and 2.0 liters of water were slowly added to remove the acid catalyst as a lower layer. After settling, the lower layer was removed and discarded. Care was taken not to agitate the mixture of added water and the reaction mixture, otherwise a stable emulsion developed.

The separated reaction mixture, i.e., the upper layer in the separatory funnel, was returned to the reaction flask and heated to 115° C. to remove residual water, which was collected in the Barrett trap. The reaction mixture was cooled to room temperature and anhydrous aluminum chloride (118 g) was slowly added. After 15 minutes of stirring, the reaction mixture was quenched by first adding 500 ml of methanol, followed by 1.0 liter of water. The reaction mixture was returned to the separatory funnel and the lower, aqueous layer was removed and discarded. Most of the excess o-xylene was removed by distillation at atmospheric pressure, and the last traces of o-xylene were removed by distillation under a vacuum of 20 mm Hg (i.e. water pump pressure). The product mixture of dixylylmethanes was distilled at 140° C. at a pressure of 0.1–0.05 mm Hg. This total procedure was repeated three more times and the combined product of distilled dixylylmethane isomers weighed 6,966.1 g and was a 91:9 mixture of 3,3',4,4'- and 2,3',3,4'-dixylymethanes.

The distilled product mixture crystallized after standing overnight. The solid portion of the crystallized mixture was separated from any remaining liquid by vacuum filtration. The liquid portion, which consisted of approximately 66% 3,3'4,4'- and 2,3',3,4'- 34% dixylylmethane, was reacted (isomerized) using o-xylene (approx. 10 moles of o-xylene per mole of dixylymethane) and a catalytic amount of anhydrous aluminum chloride (0.1 mole of aluminum chloride per mole of dixylylmethane). The resulting 3,3'4,4'-dixylylmethane, after a quenching step, was isolated as described above.

Total crystalline 3,3'4,4'-dixylylmethane (96.5% pure) isolated from the four reactions weighed 6,271.4 grams which is a 67% yield based on added formaldehyde. The 3,3',4,4'-dixylylmethane was characterized by $^{13}C$ and proton nmr spectroscopy.

EXAMPLE 12

Preparation of 1,3,3,6-Tetramethyl-1-p-Tolyl Indan by Alpha-4-Dimethyl Styrene Dimerization Alpha-4-dimethyl styrene (132 grams) was dissolved in 212 grams of o-xylene. To the resulting solution was added 10 grams of phosphoric acid.

The resulting reaction mixture was heated with agitation at 60° C. for 30 minutes. 1,3,3,6-tetramethyl-1-p-tolyl indan was formed in 95% yield. The reaction mixture was separated from the phosphoric acid catalyst, washed and neutralized.

EXAMPLE 13

Preparation of 1,3,3,6-Tetramethyl-1-o-xylyl Indan by Transaralkylation

The solution of 1,3,3,6-tetramethyl-1-p-tolyl indan of Example 12 was diluted with additional o-xylene sufficient to provide a 20-fold molar excess of o-xylene relative to 1,3,3,6-tetramethyl-1-p-tolyl indan. The excess o-xylene contains dissolved therein sufficient $AlCl_3.HCl$ to provide 20 mole percent of this catalyst in the resulting solution.

After several hours, an equilibrium distribution of 1,3,3,6-tetramethyl-1-p-tolyl indan and 1,3,3,6-tetramethyl-1-o-xylyl indan in a gas chromatography area percent ratio of 26/56 was obtained. The compounds were identified by parent ion molecular weights as determined by mass spectroscopy. The yield of 1,3,3,6-tetramethyl-o-xylyl indan was approximately 60% based on 1,3,3,6-tetramethyl tolyl indan starting material.

EXAMPLE 14

Distillation of Transaralkylated Mixture Containing DXP

The reaction product produced by the procedure described in Example 5 contains, besides DXP and PXP, diphenyl propane and a variety of indans. To first separate PXP for recycle and then isolate a DXP stream having a high purity, a batch distillation in a high temperature distillation unit was carried out. Since batch distillations typically take 10-20 hours to complete, and since DXP has a high boiling point requiring high reboiler temperatures, it was decided to remove as much of the chlorine (1260 ppm) in the quenched reaction mixture as possible prior to distillation to prevent formation of indans and/or heavy impurities. Thus, the mixture was washed with 8 parts of water at 95° C. (203° F.) for 45 minutes, which reduced the chlorine level from 1260 ppm to 131 ppm.

The scrubbed material was then transferred to the distillation unit where light material, such as o-xylene, was removed at 100 mm Hg and 150° F. (66° C.). Pressure was then reduced to 25 mm Hg and the mixture fractionated at a 5:1 reflux ratio to remove most of the phenylxylyl propane. This left 500 gms of material in the bottoms flask which was found to have a composition of 88 weight percent dixylyl propane.

Results for each cut (or fraction recovered) are listed in Table II (below). The next day further fractionation of this material at 25 mm Hg and a 10:1 reflux ratio yielded several cuts of 98 to 99 percent pure dixylyl propane. The overhead temperature during this operation was 419° F. (216° C.) and the bottoms temperature ranged from 450° to 580° F. (232° to 304° C.). Analysis of the bottoms material left in the reboiler at the end of the first day (Cut #9) by gas chromatography showed no evidence of new indan formation even though the reboiler temperature exceeded 450° F. (232° C.) for two hours. This indicates that the DXP was quite stable thermally in the presence of over 100 ppm of chlorine. At the higher temperatures encountered the next day, a slight amount of degradation to indan was observed in cuts 6A and 7A. The bottoms, however, contained almost no DXP, indicating extensive reaction above 550° F. (288° C.).

The data in Table II provides estimates of the boiling point of two key components, as follows:

|  | Boiling Point @ 25 mm Hg. F. (°C.) |
|---|---|
| 2-phenyl-2-xylyl propane | 380° (193°) |
| 2,2-dixylyl propane | 419° (216°) |

The difference in boiling point, and the thermal stability of DXP below 550° F. (288° C.), makes it possible to recover most of the DXP in high purity, even using batch distillation units employing hot oil systems to supply heat to the reboiler which characteristically operate at a maximum temperature below 550° F. (288° C.). Over half of the DXP distillation cuts exceeded 95 percent purity. Of the remainder, most were above 80 percent purity.

TABLE II

Distillation of Dixylyl Propane[1,2]

| Recovered Cut No. | Weight[3] gms | Temp. F. | Temp. C. | Area % Dimethyl Cumene | Penta Methyl Indane | Diphenyl Propane | Phenyl xylyl Propane | Dixylyl Propane | O-xylene |
|---|---|---|---|---|---|---|---|---|---|
| 1 | 62.6 | 155 | 69 | | | | | | 100 |
| 2 | 58.7 | 240 | 116 | 96.4 | | | | | |
| 3 | 69.4 | 326 | 164 | 18.0 | 57.0 | 10.5 | | | |
| 4 | 71.5 | 365 | 179 | | 24.8 | 33.4 | 32.4 | | |
| 5 | 142.0 | 375 | 190 | | 3.3 | 13.7 | 79.6 | | |
| 6 | 130.2 | 381 | 194 | | | 2.8 | 94.2 | 0.8 | |
| 7 | 174.7 | 415 | 213 | | | | 50.5 | 43.0 | |
| 8 | 64.3 | 417 | 214 | | | | 15.6 | 79.3 | |
| 9 | 499.5 | Bottoms | | | | | 1.3 | 88.3 | |
|  | 1272.9 | | | | | | | | |
|  |  |  |  | End of Day 1 |  |  |  |  |  |
|  |  |  |  | Start of Day 2 |  |  |  |  |  |
| 1A | 56.7 | 419 | 216 | | | | 9.7 | 85.2 | |
| 2A | 86.5 | 419 | 216 | | | | 1.2 | 96.1 | |
| 3A | 87.1 | 419 | 216 | | | | | 98.5 | |
| 4A | 64.1 | 419 | 216 | | | | | 99.4 | |
| 5A | 46.7 | 419 | 216 | | | | | 99.4 | |
| 6A | 24.7 | 416 | 213 | | 0.7 | | | 98.2 | |
| 7A | 28.4 | 418 | 215 | | 1.6 | | | 90.4 | |
| 8A | 92.8 | Bottoms | | | | | | 0.7 | |
|  | 487.0 | | | | | | | | |

Table III footnotes:
[1]High temperature batch distillation unit. 20 tray, 1" diameter Oldershaw column, having about 8 theoretical stages.
[2]25 mm Hg absolute pressure 10:1 Reflux Ratio.
[3]Starting weight = 1348 gms.
[4]GC Analysis.

EXAMPLE 15

Crystallization to Improve Purity of DXP

A purity for DXP which is at least about 98 percent is preferred for the oxidation of DXP to produce di(3,4-dicarboxy) phenyl propane. A simple crystallization process was used to upgrade all of the distillation cuts of the preceding Example 14 to this purity level.

Since DXP was found to be conveniently oxidized in an acetic acid solvent, acetic acid was used as the solvent for this crystallization.

The DXP from each distillation was dissolved in three parts by weight 95 percent acetic acid and heated to 185° F. (85° C.) with stirring. Continuing stirring, the solution was cooled to 32° F. (0° C.) whereupon DXP crystals form after about five minutes and the temperature sharply rises to 45° F. (7° C.). Stirring was continued ten minutes after which the slurry was centrifuged at 5000 rpm for one hour and dried. Starting, for example, with 88 percent DXP, a 99+ percent purity was achieved at 90 percent yield.

EXAMPLE 16

Three Step Process for Preparation of DXP

In a first step, 2-phenyl-2-chloropropane (PCP) was prepared by dissolving alpha methyl styrene (AMS) (3 moles) in o-xylene (7.5 moles) and sparging dry HCl (4 moles) through the chilled mixture until quantitative conversion of the AMS to 2-phenyl-2-chloropropane was achieved in about 90 minutes at 45° F. (7° C.). The reaction was exothermic. HCl addition was monitored by means of a gas bubbler on the outlet of the 12 liter reactor. When conversion was complete, no further absorption or reaction of HCl took place in the reactor and HCl was then observed in the bubbler. This technique was found to be very reproducible as evidenced by weighing the HCl cylinder at the beginning and at the end of the reaction. Since the reaction was exothermic, the rate of HCl addition during reaction was determined by the desired operating temperature. At 45° F. (7° C.) about 1.3 moles of HCl were fed to the reactor per mole of AMS. Part of this HCl was absorbed by the o-xylene.

In a second step, 2,2-phenylxylylpropane (PXP) was prepared by adding 440 ml. of o-xylene to 13.2 g AlCl$_3$ and then mixing in 11.2 g of nitromethane to produce a homogeneous solution identified as feedstream A. Feedstream A was pumped into the reactor along with feedstream B (the mixture produced in the above described first step) and comprised of PCP in o-xylene). A pump A was calibrated to deliver 30 ml/min and a pump B to deliver 450 ml/min. With foaming and the vortex induced by rapid stirring, the average capacity for the reactor was approximately 330 ml and the average residence time about 40 secs. Solution B ($\leq$25° F.) (−4° C.) and solution A were pumped at the above rates into a mixing reactor as shown in FIG. 1. The overflow of reaction product was allowed to pass into a quench tank containing 500 ml of water which was rapidly agitated by a mechanical stirrer. Vent gas was scrubbed from both reactor and quench tank. The product was washed with 3-500 ml portions of distilled water to remove AlCl$_3$ and HCl. A PXP yield of greater than 95 weight percent was obtained. When the average residence time for reaction was reduced to approximately 5 secs., the overall selectivity to PXP approached $\geq$99 percent.

In a third step, DXP was produced by transaralkylation from the PXP mixture produced in the above described second step. Such mixture was diluted to a 10:1 o-xylene to PXP mole ratio, based on the original 3 moles of AMS. Thus, another 2390 gms of o-xylene were added. Prior to such dilution, any residual water and nitromethane may be removed, although the mixture need not be bone dry. Then, 0.2 molar equivalents of AlCl$_3$ (81 gms), based on the original 3 moles of AMS were added. The procedure involved saturating the PXP mixture with HCl by purging in dry HCl gas for approximately 30 minutes. The dry AlCl$_3$ was then added over a 15 minute period at room temperature. No heat was evolved. The subsequent reaction to form DXP proceeded at room temperature and was not noticeably exothermic. About four hours were needed to reach 70-75 percent PXP conversion. During this time nitrogen and HCl were sparged into the reaction mixture. When PXP conversion had reached approximately 75 percent, the reaction mixture was quenched with 500 ml of methanol added over a one-half hour period, while purging with nitrogen. This was followed by 100 ml of distilled water, again taking one-half hour. Both quenches were exothermic and temperature was controlled in the 60° to 70° F. (15.6° to 21.1° C.) range.

Finally, the reaction mixture was washed to reduce chloride to less than 50 ppm. Molar yield of DXP, as determined by GC area ratio, was approximately 45 percent.

The DXP product was purified and the o-xylene solvent removal was carried out in a semi-continuous rotovap operated at 15 mm Hg absolute pressure and 260° F. (126° C.). Then, the o-xylene-free reaction mixture was batch distilled at 25 mm Hg and a 1:1 reflux ratio in a 1"×3' vacuum-jacketed glass column filled with ⅛" "PRO-PAK" metal ribbon packing. A 415° F. (213° C.) overhead temperature was measured during DXP withdrawal. Reboiler temperature ranged from 450° to 500° F. (232° to 260° C.)

Approximately 75 percent of the DXP cuts exceeded 95 percent purity. Of the remainder, most were above 80 percent. Assuming a purity of 98 percent was needed for the oxidation, the simple crystallization process of Example 15 was suitable for upgrading all of the distillation cuts to this level.

PXP was also recovered during the distillation (380° F. (193° C.) at 25 mm Hg) and was recycled to make DXP. High purity PXP was found to be not required for recycle. The presence of indan impurities accompanying the PXP recycle did not affect DXP yield.

The DXP cuts from the distillation were dissolved in 3 parts by weight of 95 percent acetic acid and heated to 185° F. (85° C.) with stirring. While continuing stirring, the solution was cooled to 32° F. (0° C.). After about 5 minutes at 32° F. (0° C.), DXP crystals precipitated out and the temperature rose to 45° F. (7.22° C.). Stirring was continued for 10 minutes after which the slurry was centrifuged at 5000 rpm for one hour and dried. Starting with 88 percent DXP, a 99+ percent purity at 90 percent yield was achieved.

The foregoing specification is intended as illustrative and is not to be taken as limiting. Still other variations within the spirit and the scope of the invention are possible and will readily present themselves to those skilled in the art.

We claim:

1. A process for transaralkylating a bis(aryl)alkane which process comprises contacting, under liquid phase conditions, said bis(aryl)alkane with a molar excess of an alkyl-substituted aromatic compound having different alkyl substitution from at least one of the aryl groups of said bis(aryl)alkane, said contacting being carried out in the presence of a catalytically effective amount of a Friedel-Crafts catalyst for a time period sufficient to replace at least some of said aryl groups of said bis(aryl)alkane with said alkylsubstituted aromatic, wherein said bis(aryl) alkane is characterized by the formula:

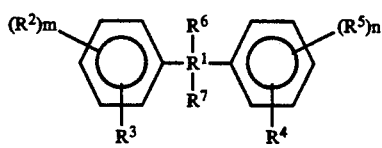

and wherein:
$R^1$ is a carbon atom,
$R^2$ and $R^5$ are each a lower alkyl radical,
$R^3$, $R^4$ and $R^6$ are each independently selected from the group consisting of hydrogen and a lower alkyl radical, $R^7$ is a lower alkyl radical and when $R^3$ is in the 2-position in said formula, $R^3$ and $R^7$ together are optionally an alkylene radical containing up to four carbons, inclusive, and m and n each is an integer having a value of 0 through 4, inclusive.

2. The process of claim 1 wherein said alkyl-substituted aromatic compound is characterized by the formula:

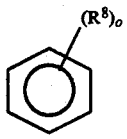

wherein:
$R^8$ is a lower alkyl group, and
o is an integer having a value of 1 through 5, inclusive.

3. The process of claim 1 wherein, in said formula, $R^1$ is methylene, $R^2$ and $R^3$ are each methyl, $R^4$ is hydrogen, $R^6$ and $R^7$ are each methyl, m is 1 and n is 0.

4. The process of claim 1 wherein said bis(aryl)alkane is a 2,2-diaryl propane and wherein each aryl group is optionally substituted by one to four lower alkyl groups.

5. The process of claim 4 wherein said starting 2,2 diaryl propane is 2-phenyl-2-(3',4'-dimethyl)phenyl propane and said alkyl-substituted aromatic compound is o-xylene.

6. The process of claim 1 wherein, in said formula, $R^2$ is methyl, $R^4$ is methyl, $R^6$ is methyl, $R^3$ is in the 2-position and $R^3$ and $R^7$ together form 2,2-dimethylethylene, and m is 1 and n is 0.

7. The process of claim 1 wherein said bis(aryl)alkane is a 1,3,3-trimethyl-1-phenyl indan and wherein both the indan phenyl group and the 1-phenyl group are each optionally substituted by one to four methyl groups.

8. The process of claim 7 wherein said 1,3,3-trimethyl-1-phenyl indan has the same corresponding methyl groups symmetrically substituted on each of its indan phenyl group and its 1-phenyl group.

9. The process of claim 8 wherein said starting 1,3,3-trimethyl-1-phenyl indan comprises 1,3,3,6-tetramethyl-1-p-tolyl indan.

10. The process of claim 1 wherein said molar excess of said alkyl-substituted aromatic compound is at least about 10 times the molar quantity of said starting compound.

11. The process of claim 1 wherein said catalyst comprises a mixture of aluminum chloride and hydrogen chloride.

12. The process of claim 1 wherein said alkyl-substituted aromatic compound is o-xylene.

13. A process for transaralkylating a starting 1,3,3-trialkyl-1-aryl-substituted indan wherein the 1-aryl group can optionally be substituted with from 1 to 4 lower alkyl groups to produce a product 1,3,3-trialkyl-1-aryl-substituted indan having a different 1-aryl group than said starting 1,3,3-trialkyl-1aryl substituted indan, said process comprising contacting said starting substituted indan with a molar excess of a lower alkyl-substituted aromatic compound which has a different lower alkyl substitution from said alkyl-substitution present in said 1-aryl group of said starting 1,3,3-trialkyl-1-aryl-substituted indan, under liquid phase conditions in the presence of a catalytically effective amount of a catalyst comprising aluminum trichloride and hydrogen chloride until at least some of said alkyl-substituted aromatic compound has replaced at least a portion of said 1-aryl group of said starting 1,3,3-trialkyl-1-aryl-substituted indan.

14. The process of claim 13 wherein said starting substituted indan has the same substituent alkyl groups substituted on each of its indan aryl group and its 1-aryl group.

15. The process of claim 13 wherein said molar excess of said alkyl-substituted aromatic compound is at least about 10 times the molar quantity of said starting substituted indan, and wherein the 3-position of said starting substituted indan is substituted by two methyl groups.

16. The process of claim 13 wherein said starting indan is 1,3,3,6-tetramethyl-1-p-tolyl indan, said product indan is 1,3,3,6-tetramethyl-1o-xylyl indan and said lower alkyl-substituted aromatic compound is o-xylene.

17. A process for producing 2,2-di(alkyl-substituted)aryl propane from alpha methyl styrene comprising the steps of
(A) hydrochlorinating alpha methyl styrene to produce a 2-phenyl-2-chloropropane,
(B) alkylating an alkyl-substituted aromatic compound with said 2-phenyl-2-chloropropane in the presence of both a catalytically effective amount of a Friedel-Crafts catalyst comprised of an adduct of aluminum trichloride and nitromethane, and also a molar excess of said aromatic compound to produce 2-phenyl-2-(alkyl-substituted)aryl propane, and
(C) transaralkylating said 2-phenyl-2-(alkyl-substituted)aryl propane with said alkyl-substituted aromatic compound in the presence of both a catalytically effective amount of a catalyst comprised of aluminum trichloride and hydrogen chloride and also a molar excess of said alkyl-substituted aromatic compound until at least some of said 2,2-di(alkyl-substituted)aryl propane is produced.

18. The process of claim 17 wherein said alkylation is conducted at a temperature in the range of about $-5°$ C. to about 50° C. until equilibrium conditions are reached.

19. The process of claim 17 wherein said 2,2-di(alkyl-substituted)aryl propane is 2,2-dixylyl propane, said alkyl-substituted aromatic compound is o-xylene, and said 2-phenyl-2-(alkyl-substituted) aryl propane is 2-phenyl-2-xylyl-propane.

20. The process of claim 19 wherein said alkylating is carried out by continuously admixing said 2-phenyl-2-chloro propane and said catalyst in the presence of said o-xylene, the rate of said admixing being such that the evolution of hydrogen chloride gas occurs at a controlled rate.

21. The process of claim 19 wherein said transaralkylating is conducted at a temperature in the range of about 0° C. to about 80° C. until equilibrium conditions are reached.

22. The process of claim 19 wherein said alkylating is continuous, comprising the steps of simultaneously:
introducing into a mixing zone a first feedstream comprised of 2-phenyl-2-chloropropane dissolved in o-xylene,
introducing into said mixing zone a second feedstream comprised of a 1:2 molar ratio adduct of aluminum trichloride and nitromethane dissolved in o-xylene,
admixing the resulting mixture in said mixing zone, maintaining the rate of said introducing of said 2-phenyl-2-chloro propane into said mixing zone and the weight ratio of said adduct to said 2-phenyl-2-chloro propane such that gaseous hydrogen chloride is evolved from said resulting mixture at a controlled rate, separating said so evolved hydrogen chloride from said mixing zone, cooling said mixing zone to maintain the temperature of said resulting mixture in the range of about −5° C. to about 50° C., and removing from said mixing zone a o-xylene solution containing dissolved therein 2-phenyl-2-xylyl propane.

23. The process of claim 22 wherein said first and said second feedstreams are each at a temperature below about 50° C. preceding said introducing.

24. The process of claim 22 wherein said first feedstream comprises on a 100 weight percent basis about 1 to about 50 weight percent of said 2-phenyl-2-chloro propane with the balance up to 100 weight percent thereof being said o-xylene.

25. The process of claim 22 wherein said second feedstream comprises on a 100 weight percent basis about 0.05 to about 20 weight percent of said aluminum chloride, sufficient nitromethane to provide a mole ratio of aluminum chloride to nitromethane of about 1:2, with the balance up to 100 weight percent thereof being said o-xylene.

26. A process for producing a 1,3,3-trimethyl-1-aryl indan comprising the steps of (A) dimerizing a compound selected from the group consisting of alpha methyl styrene and a lower alkyl-substituted alpha methyl styrene in the presence of a catalytically effective amount of an acid catalyst to form a 1,3,3-trimethyl-1-phenyl indan, and (B) transaralkylating said 1,3,3-trimethyl-1-phenyl indan with an alkyl-substituted aromatic compound in the presence of both a catalytically effective amount of a Friedel-Crafts catalyst, and also a molar excess of said aromatic compound to form a 1,3,3-trimethyl-1-(lower alkyl-substituted)phenyl indan.

27. The process of claim 26 wherein said 1,3,3-trimethyl-1-aryl indan is 1,3,3,6-tetramethyl-1-o-xylyl indan, said compound is alpha-4-dimethyl styrene, said alkyl-substituted aromatic compound is o-xylene and said Friedel-Crafts catalyst comprises aluminum trichloride and hydrogen chloride.

28. A process for preparing 3,3',4,4'-dixylylmethane comprising: reacting in a suitable reaction zone a reaction mixture comprising o-xylene, a dixylylmethane isomer selected from 2,2',3,3'-, 2,3',3,4'-dixylylmethane, and mixtures thereof, and a catalytically effective amount of Friedel-Crafts catalyst, for a time sufficient to convert a substantial portion of said isomer to 3,3',4,4'-dixylylmethane product.

29. The process of claim 28 wherein said Friedel-Crafts catalyst is aluminum trichloride and said aluminum trichloride is present in said reaction mixture in an amount of about 2 to about 20 mole percent based on the amount of said isomer present.

* * * * *